US006322965B1

(12) United States Patent
Yamaguchi et al.

(10) Patent No.: US 6,322,965 B1
(45) Date of Patent: Nov. 27, 2001

(54) CHIMERA ANTIGEN PEPTIDE

(75) Inventors: Kenjiro Yamaguchi; Tomiko Kashiwakuma; Yukie Chiba; Shintaro Yagi; Akira Hasegawa, all of Saitama (JP)

(73) Assignee: Advanced Life Science Institute, Inc., Saitama (JP)

( * ) Notice: Subject to any disclaimer, the term of this patent is extended or adjusted under 35 U.S.C. 154(b) by 0 days.

(21) Appl. No.: 09/020,846

(22) Filed: Feb. 9, 1998

(30) Foreign Application Priority Data

Feb. 10, 1997 (JP) ................................... 9-027015

(51) Int. Cl.$^7$ ............................ C12Q 1/68; A61K 39/29
(52) U.S. Cl. .................. 435/5; 530/350; 530/806; 530/826; 435/7.1; 435/69.1; 435/69.3; 435/69.7; 435/440; 435/455; 435/471; 436/501; 436/536; 436/811; 436/820; 536/23.1; 536/23.4; 536/23.72
(58) Field of Search .................... 530/350, 806, 530/826; 435/69.1, 320.1, 5, 7.1, 69.3, 69.7; 436/501, 536, 811, 820; 536/23.1, 23.4, 23.72

(56) References Cited

U.S. PATENT DOCUMENTS 5,683,695 * 11/1997 Shen et al. .................. 424/185.1
5,756,312 * 5/1998 Weiner et al. .................. 435/69.3

FOREIGN PATENT DOCUMENTS

08073497 * 3/1996 (JP) .

OTHER PUBLICATIONS

Yagi et al. 1996 Biological and Pharmaceutical Bulletin 19 (10) 1254–1260.*

Y. Khudyakof et al., Artificial Mosaic Protein Containing Antigenic Epitopes of Hepatitis E Virus, J. of Virology, Nov. 1994, vol. 68:11, p. 7067–7074.

V. Kumar et al. Hepatitis B virus envelope epitomes: gene assembly and expression in *Escherichia coli*, Gene. 110 (1992) p. 137–144.

D.Y. Chien et al., Diagnosis of hepatitis C virus (HCV) infection using an immunodominant chimeric polyprotein to capture circulating antibodies, Nov. 1992, Proc. Natl. Acad. Sci. V.89 pp 10011–10015.

* cited by examiner

Primary Examiner—Mary K. Zeman
(74) Attorney, Agent, or Firm—Foley & Lardner

(57) ABSTRACT

A chimera antigen peptide containing the epitope regions in the core region, the NS3 region, and the NS4 region of the HCV polypeptide. A sensitive detection of a wide range of infection by hepatitis C virus (HCV) can be carried out.

19 Claims, No Drawings

SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
      (A) LENGTH: 1278 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "Synthetic DNA"

(ix) FEATURE:
      (A) NAME/KEY: CDS
      (B) LOCATION: 7..1269

(xi) SEQUENCE DESCRIPTION: SEQ ID NO:1:

```
ATCGAT ATG AAA GCT ATC TTC GTT CTG AAA GGT TCT CTG GAC CGT GAC        48
       Met Lys Ala Ile Phe Val Leu Lys Gly Ser Leu Asp Arg Asp
         1               5                  10

CCA GAA TTC ACT AAA GTG CCG GCT GCA TAT GCA GCC CAA GGG TAC AAG       96
Pro Glu Phe Thr Lys Val Pro Ala Ala Tyr Ala Ala Gln Gly Tyr Lys
 15              20                  25                  30

GTG CTC GTC CTC AAC CCG TCC GTT GCC GCC ACC TTA GGT TTT GGA GCG      144
Val Leu Val Leu Asn Pro Ser Val Ala Ala Thr Leu Gly Phe Gly Ala
                 35                  40                  45

TAT ATG TCT AAG GCA CAT GGC ACC GAC CCC AAC ATC AGA ACT GGG GTA      192
Tyr Met Ser Lys Ala His Gly Thr Asp Pro Asn Ile Arg Thr Gly Val
             50                  55                  60

AGG ACT ATC ACC ACA GGC GCC CCC ATC ACG TAC TCC ACC TAC GGC AAG      240
Arg Thr Ile Thr Thr Gly Ala Pro Ile Thr Tyr Ser Thr Tyr Gly Lys
         65                  70                  75

TTC CTT GCC GAC GGT GGT TGT TCT GGG GGC GCT TAT GAC ATC ATA GGG      288
Phe Leu Ala Asp Gly Gly Cys Ser Gly Gly Ala Tyr Asp Ile Ile Gly
     80                  85                  90

TCC GGA GAG GAG GTG GCC CTG TCT AAC ACT GGA GAG ATC CCC TCC TAT      336
Ser Gly Glu Glu Val Ala Leu Ser Asn Thr Gly Glu Ile Pro Ser Tyr
 95                 100                 105                 110

GGC AAA GGC ATC CCC ATT GAA GTC ATC AAG GGG GGA AGG CAT CTC ATT      384
Gly Lys Gly Ile Pro Ile Glu Val Ile Lys Gly Gly Arg His Leu Ile
                115                 120                 125

TTC TGC CAT TCC AAG AAG AAG TGC GAC GAG CTC GCC GCG AAG TTG TCA      432
Phe Cys His Ser Lys Lys Lys Cys Asp Glu Leu Ala Ala Lys Leu Ser
            130                 135                 140

GGC CTC GGG ATT AAT GCT GTG GCA TAC TAC CGG GGT CTT GAT GTG TCC      480
Gly Leu Gly Ile Asn Ala Val Ala Tyr Tyr Arg Gly Leu Asp Val Ser
        145                 150                 155

GTC ATA CCG ACC AGC GGA GAC GTC GTT GTC GTG GCA ACA GAC GCT CTA      528
Val Ile Pro Thr Ser Gly Asp Val Val Val Val Ala Thr Asp Ala Leu
    160                 165                 170

ATG ACG GGC TAT ACC GGC GAT TTT GAC TCA GTG ATC GAC TGT AAC ACA      576
Met Thr Gly Tyr Thr Gly Asp Phe Asp Ser Val Ile Asp Cys Asn Thr
175                 180                 185                 190

TGC GTC ACC CAG GGA TCT GGA CTG GTA AGC TTC GCC TCA CAC CTC CCT      624
Cys Val Thr Gln Gly Ser Gly Leu Val Ser Phe Ala Ser His Leu Pro
                195                 200                 205

TAC ATC GAA CAG GGA ATG CAG CTT GCC GAG CAA TTC AAG CAG AAG GCG      672
Tyr Ile Glu Gln Gly Met Gln Leu Ala Glu Gln Phe Lys Gln Lys Ala
```

```
                  210                 215                 220
CTC GGA TTG CTG CAA ACA GCC ACC AAG CAC GCG GAG GCT GCT GCT CCC     720
Leu Gly Leu Leu Gln Thr Ala Thr Lys His Ala Glu Ala Ala Ala Pro
            225                 230                 235

GTG GTA GGT ACC CCT AAA GCT CGT CGT CCG GAA GGT CGT GCT TGG GCT     768
Val Val Gly Thr Pro Lys Ala Arg Arg Pro Glu Gly Arg Ala Trp Ala
    240                 245                 250

CAA CCC GGG AGT GTG GTC ATT GTG GGT AGG ATC ATC TTG TCC GGG AGG     816
Gln Pro Gly Ser Val Val Ile Val Gly Arg Ile Ile Leu Ser Gly Arg
255                 260                 265                 270

CCG GCT GTT ATT CCC GAC AGG GAA GTC CTC TAC CGG GAG TTC TTT CTC     864
Pro Ala Val Ile Pro Asp Arg Glu Val Leu Tyr Arg Glu Phe Phe Leu
            275                 280                 285

GAG GCC TCT AGA GCG GCT CTC ATT GAA GAG GGG CAA CGG ATA GCC GAG     912
Glu Ala Ser Arg Ala Ala Leu Ile Glu Glu Gly Gln Arg Ile Ala Glu
        290                 295                 300

ATG CTG AAG TCC AAG ATC CAG GGC TTA CTG CAG CAA GCC TCC AAG CAG     960
Met Leu Lys Ser Lys Ile Gln Gly Leu Leu Gln Gln Ala Ser Lys Gln
    305                 310                 315

GCC CAA GAC ATA AAA ATC GAC GGT ACC CTG ATT ATT CCG AAA GAT CGT    1008
Ala Gln Asp Ile Lys Ile Asp Gly Thr Leu Ile Ile Pro Lys Asp Arg
320                 325                 330

CGC AGC ACC GGT AAA AGC TGG GGT AAA CCG GGC TTC CTC ATC GAT AGC    1056
Arg Ser Thr Gly Lys Ser Trp Gly Lys Pro Gly Phe Leu Ile Asp Ser
335                 340                 345                 350

TTG CAT ATC AAC CAG CGA GCC GTC GTT GCA CCG GAC AAG GAG GTC CTT    1104
Leu His Ile Asn Gln Arg Ala Val Val Ala Pro Asp Lys Glu Val Leu
            355                 360                 365

TAT GAG GCT TTT GAT GAG ATG GAG CTC GCC ATG GGC ATG GGC ACG AAT    1152
Tyr Glu Ala Phe Asp Glu Met Glu Leu Ala Met Gly Met Gly Thr Asn
        370                 375                 380

CCT AAA CCT CAA AGA AAA ACC AAA AGA AAC ACT AAC CGT CGC CCA CAA    1200
Pro Lys Pro Gln Arg Lys Thr Lys Arg Asn Thr Asn Arg Arg Pro Gln
    385                 390                 395

GAC GTT AAG TTT CCG GGC GGC GGC CAG ATC GTT GGC GGA GTA TAC TTG    1248
Asp Val Lys Phe Pro Gly Gly Gly Gln Ile Val Gly Gly Val Tyr Leu
400                 405                 410

TTG CCG CGC AGG GGC CCC AGA TAAGGATCC                              1278
Leu Pro Arg Arg Gly Pro Arg
415                 420

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Phe Arg Gln Pro Ile Pro Lys Ala Arg Arg Pro Glu Gly Arg Thr Trp
1               5                   10                  15

Ala Gln Pro Gly
            20

(2) INFORMATION FOR SEQ ID NO:3:

(i) SEQUENCE CHARACTERISTICS:
        (A) LENGTH: 20 amino acids
        (B) TYPE: amino acid
```

(C) STRANDEDNESS:
        (D) TOPOLOGY: linear (ii) MOLECULE TYPE: peptide (xi) SEQUENCE DESCRIPTION: SEQ ID NO:3:

Arg Arg Gln Pro Ile Pro Lys Asp Arg Arg Ser Thr Gly Lys Ser Trp
1               5                  10                  15
Gly Lys Pro Gly
            20

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:4:

GCGAATTCCA GTCATTCCAA GTGGCCCAT                                    29

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

CAGGATCCTT ACCCAGTTCT GATGTTGGG                                    29

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

GCGAATTCGG AGCGTATATG TCTAAG                                       26

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:7:

CAGGATCCTT AGCCGATGCC CAAGATGGA                                    29

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:8:

GCGAATTCGG CGCTTATGAC ATCATA                                              26

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:9:

CAGGATCCTT ATCCAGTGTT AGACAGGGC                                           29

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:10:

GCGAATTCGG AGCACGGCTC GTCGTG                                              26

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:11:

CAGGATCCTT ATGACAACTT CGCGGCGAG                                           29

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Sythetic DNA"

(xi) SEQUENCE DESCRIPTION: SEQ ID NO:12:

GCGAATTCGG AAGGCATCTC ATTTTC                                              26

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:13:

CAGGATCCTT AGCCCGTCAT ATGAGCGTC                                    29

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:14:

GCGAATTCGG CCTCGGGATT AATGCT                                      26

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:15:

CAGGATCCTT ACTCAATGGT GAAGGTGGG                                    29

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:16:

GCGAATTCGC CTCACACCTC CCTTACATC                                    29

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:17:

GGGTACCTAC CACGGGAGCA GCAGCTC                                      27

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:18:

```
AGGTACCCCT AAAGCTCGTC GTCCGGAAGG TCGTGCT                    37
```

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:19:

```
TCCCGGGTTG AGCCCAAGCA CGACCTTCCG GACG                       34
```

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:20:

```
ACCCGGGAGT GTGGTCATTG TGGGTAGG                              28
```

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:21:

```
GAGGATCCTT ATCAATCGAA CTCCCGGTAG AGGACTTC                   38
```

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:22:

```
GTAAGCTTCG CCTCACACCT CCCTTACATC                            30
```

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:23:

```
GCCTCGAGAA AGAACTCCCG GTAGAGGAC                                  29
```

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:24:

```
ATGGAGCTCG CCATGGGCAT GGGCACGAAT                                 30
```

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:25:

```
TATGGATCCT TATCTGGGGC CCCTGCGCGG CAA                             33
```

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:26:

```
CCAGCCTTCA CTAAAGTGCC GGCTGCA                                    27
```

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:27:

```
CTCTCCGGAC CCTATGATGT CATAAGCGCC                                30
```

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:28:

```
GGGTCCGGAG AGGAGGTGGC CCTGTCT                                   27
```

(2) INFORMATION FOR SEQ ID NO:29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:29:

```
GAAGCTTACC AGTCCAGATC CCTGGGTGAC GCATCTGTTA CA                  42
```

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:30:

```
GACTCGAGGC CTCTAGAGCG GCTCTCATT                                 29
```

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:31:

```
GCTATCGATT TTTATGTCTT GGGCCTG                                   27
```

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:32:

AAAATCGATA GCTTGCATAT CAACCAG                                    27

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:33:

GACGAGCTCC ATCTCATCAA AAGCCTC                                    27

(2) INFORMATION FOR SEQ ID NO:34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:34:

CGGTCGACGG TACCCTGATT ATTCCGAAAG ATCGTCGCAG CACCGGTA             48

(2) INFORMATION FOR SEQ ID NO:35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:35:

GCTATCGATG AGGAAGCCCG GTTTACCCCA GCTTTTACCG GTGCTGCG             48

(2) INFORMATION FOR SEQ ID NO:36:

(i) SEQUENCE CHARACTERISTICS:
        (A) LENGTH: 43 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Met Gly Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
                20                  25                  30
Gly Val Tyr Leu Leu Pro Arg Arg Gly Pro Arg
            35                  40

(2) INFORMATION FOR SEQ ID NO:37:

(i) SEQUENCE CHARACTERISTICS:
        (A) LENGTH: 15 amino acids
        (B) TYPE: amino acid

```
            (C) STRANDEDNESS:
            (D) TOPOLOGY: linear (ii) MOLECULE TYPE: peptide (xi) SEQUENCE DESCRIPTION: SEQ ID NO:37:

Pro Lys Ala Arg Arg Pro Glu Gly Arg Ala Trp Ala Gln Pro Gly
1               5                   10                  15

(2) INFORMATION FOR SEQ ID NO:38:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:38:

Pro Lys Asp Arg Arg Ser Thr Gly Lys Ser Trp Gly Lys Pro Gly
1               5                   10                  15

(2) INFORMATION FOR SEQ ID NO:39:

(i) SEQUENCE CHARACTERISTICS:
            (A) LENGTH: 76 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:39:

Thr Lys Val Pro Ala Ala Tyr Ala Ala Gln Gly Tyr Lys Val Leu Val
1               5                   10                  15

Leu Asn Pro Ser Val Ala Ala Thr Leu Gly Phe Gly Ala Tyr Met Ser
                20                  25                  30

Lys Ala His Gly Thr Asp Pro Asn Ile Arg Thr Gly Val Arg Thr Ile
            35                  40                  45

Thr Thr Gly Ala Pro Ile Thr Tyr Ser Thr Tyr Gly Lys Phe Leu Ala
        50                  55                  60

Asp Gly Gly Cys Ser Gly Gly Ala Tyr Asp Ile Ile
65                  70                  75

(2) INFORMATION FOR SEQ ID NO:40:

(i) SEQUENCE CHARACTERISTICS:
            (A) LENGTH: 98 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:40:

Glu Glu Val Ala Leu Ser Asn Thr Gly Glu Ile Pro Phe Tyr Gly Lys
1               5                   10                  15

Gly Ile Pro Ile Glu Val Ile Lys Gly Arg His Leu Ile Phe Cys
                20                  25                  30

His Ser Lys Lys Lys Cys Asp Glu Leu Ala Ala Lys Leu Ser Gly Leu
            35                  40                  45

Gly Ile Asn Ala Val Ala Tyr Tyr Arg Gly Leu Asp Val Ser Val Ile
        50                  55                  60
```

```
Pro Thr Ser Gly Asp Val Val Val Ala Thr Asp Ala Leu Met Thr
65                  70                  75                  80

Gly Tyr Thr Gly Asp Phe Asp Ser Val Ile Asp Cys Asn Thr Cys Val
                85                  90                  95

Thr Gln
```

(2) INFORMATION FOR SEQ ID NO:41:

(i) SEQUENCE CHARACTERISTICS:
        (A) LENGTH: 39 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Ala Ser His Leu Pro Tyr Ile Glu Gln Gly Met Gln Leu Ala Glu Gln
1               5                   10                  15

Phe Lys Gln Lys Ala Leu Gly Leu Leu Gln Thr Ala Thr Lys His Ala
                20                  25                  30

Glu Ala Ala Ala Pro Val Val
            35
```

(2) INFORMATION FOR SEQ ID NO:42:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Gly Ser Val Val Ile Val Gly Arg Ile Ile Leu Ser Gly Arg Pro Ala
1               5                   10                  15

Val Ile Pro Asp Arg Glu Val Leu Tyr Arg Glu Phe
                20                  25
```

(2) INFORMATION FOR SEQ ID NO:43:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Ala Ser Arg Ala Ala Leu Ile Glu Glu Gly Gln Arg Ile Ala Glu Met
1               5                   10                  15

Leu Lys Ser Lys Ile Gln Gly Leu Leu Gln Gln Ala Ser Lys Gln Ala
                20                  25                  30

Gln Asp Ile Lys
            35
```

(2) INFORMATION FOR SEQ ID NO:44:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Leu His Ile Asn Gln Arg Ala Val Val Ala Pro Asp Lys Glu Val Leu
1               5                   10                  15

Tyr Glu Ala Phe Asp Glu Met Glu
            20

(2) INFORMATION FOR SEQ ID NO:45:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:45:

GGAATTCGAG GAGGTGGCCC TGTCTAACAC T                              31

(2) INFORMATION FOR SEQ ID NO:46:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:46:

GGGATCCTTA CTGGGTGACG CATGTGTTAC AGTC                           34

(2) INFORMATION FOR SEQ ID NO:47:

(i) SEQUENCE CHARACTERISTICS:
        (A) LENGTH: 1197 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: CDS
        (B) LOCATION: 1..1188

(xi) SEQUENCE DESCRIPTION: SEQ ID NO:47:

GAA TTC ACC AAA GTG CCG GTT GCT TAT GCG GCC AAA GGT TAT AAG GTC    48
Glu Phe Thr Lys Val Pro Val Ala Tyr Ala Ala Lys Gly Tyr Lys Val
1               5                   10                  15

CTG GTT CTG GAC CCG AGC GTT GCC AGC ACC CTG GGT TTC GGC GCG TAT    96
Leu Val Leu Asp Pro Ser Val Ala Ser Thr Leu Gly Phe Gly Ala Tyr
            20                  25                  30

CTG AGC AAG GCC CAT GGT GTG AAC CCG AAC ATC CGC ACG GGC ATC CGT   144
Leu Ser Lys Ala His Gly Val Asn Pro Asn Ile Arg Thr Gly Ile Arg
        35                  40                  45

ACC GTT ACC ACC GGT GCT CCG GTG ACC TAT TCC ACC TAC GGT AAA TAC   192
Thr Val Thr Thr Gly Ala Pro Val Thr Tyr Ser Thr Tyr Gly Lys Tyr
    50                  55                  60

CTG GCG GAC GGC GGT TGC GCC GGC GGT GCG TAC GAT GTG ATC GGA TCT   240
Leu Ala Asp Gly Gly Cys Ala Gly Gly Ala Tyr Asp Val Ile Gly Ser

-continued

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     | 65  |     |     |     |     | 70  |     |     |     |     | 75  |     |     |     | 80  |
| GGA | GAG | GAG | GTG | GCC | CTG | TCT | AAC | ACT | GGA | GAG | GTC | CCC | TTC | TAT | GGC | 288 |
| Gly | Glu | Glu | Val | Ala | Leu | Ser | Asn | Thr | Gly | Glu | Val | Pro | Phe | Tyr | Gly |     |
|     |     |     |     | 85  |     |     |     |     | 90  |     |     |     |     | 95  |     |     |
| CGC | GCG | ATC | CCG | ATC | GAA | GCG | ATC | AAA | GGC | GGT | CGC | CAT | CTG | GTT | TTC | 336 |
| Arg | Ala | Ile | Pro | Ile | Glu | Ala | Ile | Lys | Gly | Gly | Arg | His | Leu | Val | Phe |     |
|     |     |     | 100 |     |     |     |     | 105 |     |     |     |     | 110 |     |     |     |
| TGC | CAT | AGC | AAG | GAG | AAA | TGC | GAT | GAA | CTG | GCG | AGC | GCG | CTG | TCC | GGA | 384 |
| Cys | His | Ser | Lys | Glu | Lys | Cys | Asp | Glu | Leu | Ala | Ser | Ala | Leu | Ser | Gly |     |
|     |     | 115 |     |     |     |     | 120 |     |     |     |     | 125 |     |     |     |     |
| TTG | GGT | CTG | AAC | GCT | GTG | GCA | TTC | TAT | CGC | GGT | CTG | GAC | GTG | AGC | ATT | 432 |
| Leu | Gly | Leu | Asn | Ala | Val | Ala | Phe | Tyr | Arg | Gly | Leu | Asp | Val | Ser | Ile |     |
|     | 130 |     |     |     |     | 135 |     |     |     |     | 140 |     |     |     |     |     |
| ATC | CCG | ACC | CAG | GGC | GAT | GTG | GTT | ATC | GTT | AGC | ACC | GAT | GCG | CTG | ATG | 480 |
| Ile | Pro | Thr | Gln | Gly | Asp | Val | Val | Ile | Val | Ser | Thr | Asp | Ala | Leu | Met |     |
| 145 |     |     |     |     | 150 |     |     |     |     | 155 |     |     |     |     | 160 |     |
| ACC | GGT | TTT | ACC | GGC | GAT | TTT | GAC | TCA | GTG | GTC | GAC | TGT | AAC | ACA | TGC | 528 |
| Thr | Gly | Phe | Thr | Gly | Asp | Phe | Asp | Ser | Val | Val | Asp | Cys | Asn | Thr | Cys |     |
|     |     |     |     | 165 |     |     |     |     | 170 |     |     |     |     | 175 |     |     |
| ATC | ACC | CAG | GGA | TCT | GGA | CTG | GTA | AGC | TTC | GCG | AGC | CAT | GTG | CCG | TAC | 576 |
| Ile | Thr | Gln | Gly | Ser | Gly | Leu | Val | Ser | Phe | Ala | Ser | His | Val | Pro | Tyr |     |
|     |     |     | 180 |     |     |     |     | 185 |     |     |     |     | 190 |     |     |     |
| ATC | GAG | CAG | GGT | ATG | CAA | CTG | AGC | GAA | CAA | TTT | AAG | CAG | AAG | AGC | CTG | 624 |
| Ile | Glu | Gln | Gly | Met | Gln | Leu | Ser | Glu | Gln | Phe | Lys | Gln | Lys | Ser | Leu |     |
|     |     | 195 |     |     |     |     | 200 |     |     |     |     | 205 |     |     |     |     |
| GGT | CTG | CTG | CAG | ACC | GCG | ACC | AAA | CAG | GCG | GAG | GCG | GCC | GCC | CCG | GTG | 672 |
| Gly | Leu | Leu | Gln | Thr | Ala | Thr | Lys | Gln | Ala | Glu | Ala | Ala | Ala | Pro | Val |     |
|     | 210 |     |     |     |     | 215 |     |     |     |     | 220 |     |     |     |     |     |
| GTT | GGC | ACC | CCG | AAA | AGC | CGC | CGT | CCG | GAA | GGT | CGT | GCC | TGG | GCG | CAA | 720 |
| Val | Gly | Thr | Pro | Lys | Ser | Arg | Arg | Pro | Glu | Gly | Arg | Ala | Trp | Ala | Gln |     |
| 225 |     |     |     |     | 230 |     |     |     |     | 235 |     |     |     |     | 240 |     |
| CCG | GGT | ACC | ATC | ATC | CTG | AGC | GGT | CGT | CCG | GCG | GTT | GTA | CCG | GAT | CGT | 768 |
| Pro | Gly | Thr | Ile | Ile | Leu | Ser | Gly | Arg | Pro | Ala | Val | Val | Pro | Asp | Arg |     |
|     |     |     |     | 245 |     |     |     |     | 250 |     |     |     |     | 255 |     |     |
| GAA | GTG | CTG | TAT | CAA | GAA | TTT | CTC | GAG | GCC | TCT | AGA | GCG | GCT | CTC | ATT | 816 |
| Glu | Val | Leu | Tyr | Gln | Glu | Phe | Leu | Glu | Ala | Ser | Arg | Ala | Ala | Leu | Ile |     |
|     |     |     | 260 |     |     |     |     | 265 |     |     |     |     | 270 |     |     |     |
| GAA | GAG | GGG | CAA | CGG | ATA | GCC | GAG | ATG | CTG | AAG | TCC | AAG | ATC | CAG | GGC | 864 |
| Glu | Glu | Gly | Gln | Arg | Ile | Ala | Glu | Met | Leu | Lys | Ser | Lys | Ile | Gln | Gly |     |
|     |     | 275 |     |     |     |     | 280 |     |     |     |     | 285 |     |     |     |     |
| TTA | CTG | CAG | CAA | GCC | TCC | AAG | CAG | GCC | CAA | GAC | ATA | AAA | ATC | GAC | GGT | 912 |
| Leu | Leu | Gln | Gln | Ala | Ser | Lys | Gln | Ala | Gln | Asp | Ile | Lys | Ile | Asp | Gly |     |
|     | 290 |     |     |     |     | 295 |     |     |     |     | 300 |     |     |     |     |     |
| ACC | CTG | ATT | ATT | CCG | AAA | GAT | CGT | CGC | AGC | ACC | GGT | AAA | AGC | TGG | GGT | 960 |
| Thr | Leu | Ile | Ile | Pro | Lys | Asp | Arg | Arg | Ser | Thr | Gly | Lys | Ser | Trp | Gly |     |
| 305 |     |     |     |     | 310 |     |     |     |     | 315 |     |     |     |     | 320 |     |
| AAA | CCG | GGC | TTC | CTC | ATC | GAT | AGC | TTG | CAT | ATC | AAC | CAG | CGA | GCC | GTC | 1008 |
| Lys | Pro | Gly | Phe | Leu | Ile | Asp | Ser | Leu | His | Ile | Asn | Gln | Arg | Ala | Val |     |
|     |     |     | 325 |     |     |     |     | 330 |     |     |     |     | 335 |     |     |     |
| GTT | GCA | CCG | GAC | AAG | GAG | GTC | CTT | TAT | GAG | GCT | TTT | GAT | GAG | ATG | GAG | 1056 |
| Val | Ala | Pro | Asp | Lys | Glu | Val | Leu | Tyr | Glu | Ala | Phe | Asp | Glu | Met | Glu |     |
|     |     |     | 340 |     |     |     |     | 345 |     |     |     |     | 350 |     |     |     |
| CTC | GCC | ATG | GGC | ACC | AAC | CCG | AAA | CCG | GAG | CGT | AAA | AGC | AAG | CGT | AAC | 1104 |
| Leu | Ala | Met | Gly | Thr | Asn | Pro | Lys | Pro | Glu | Arg | Lys | Ser | Lys | Arg | Asn |     |
|     |     |     | 355 |     |     |     |     | 360 |     |     |     |     | 365 |     |     |     |
| ACC | AAC | CGT | AAA | CCG | CAG | GAT | ATT | AAA | TTC | CCG | GGT | AGT | GGT | CAG | GTG | 1152 |
| Thr | Asn | Arg | Lys | Pro | Gln | Asp | Ile | Lys | Phe | Pro | Gly | Ser | Gly | Gln | Val |     |
|     | 370 |     |     |     |     | 375 |     |     |     |     | 380 |     |     |     |     |     |
| GTG | GGT | GGT | GTG | TAC | CTG | GTG | CCG | CGT | CGT | GGT | CCG | TAAGGATCC |  |  |  | 1197 |

```
Val Gly Gly Val Tyr Leu Val Pro Arg Arg Gly Pro
385                 390                 395
```

(2) INFORMATION FOR SEQ ID NO:48:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:48:

```
AGCCGTGACC CAGAATTCAC CAAAGTGCCG GTTGCTTATG CGGCCAAAGG TTATAAGGTC    60

CTGGTTCTGG ACCCGAGC                                                 78
```

(2) INFORMATION FOR SEQ ID NO:49:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:49:

```
ACCATGGGCC TTGCTCAGAT ACGCGCCGAA ACCCAGGGTG CTGGCAACGC TCGGGTCCAG    60

AACCAG                                                              66
```

(2) INFORMATION FOR SEQ ID NO:50:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:50:

```
GCCCATGGTG TGAACCCGAA CATCCGCACG GGCATCCGTA CCGTTACCAC CGGTGCTCCG    60

GTGACCTAT                                                           69
```

(2) INFORMATION FOR SEQ ID NO:51:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:51:

```
ATCGTACGCA CCGCCGGCGC AACCGCCGTC CGCCAGGTAT TTACCGTAGG TGGAATAGGT    60

CACCGGAGCA CC                                                       72
```

(2) INFORMATION FOR SEQ ID NO:52:

(i) SEQUENCE CHARACTERISTICS:

(A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:52:

GGTGCGTACG ATGTGATCTA TGGCCGCGCG ATCCCGATCG AAGCGATCAA AGGCGGTCGC    60

CATCTGGTT    69

(2) INFORMATION FOR SEQ ID NO:53:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:53:

CAATCCGGAC AGCGCGCTCG CCAGTTCATC GCATTTCTCC TTGCTATGGC AGAAAACCAG    60

ATGGCGACCG CC    72

(2) INFORMATION FOR SEQ ID NO:54:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:54:

CTGTCCGGAT TGGGTCTGAA CGCTGTGGCA TTCTATCGCG GTCTGGACGT GAGCATTATC    60

CCGACCCAGG GC    72

(2) INFORMATION FOR SEQ ID NO:55:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:55:

CGCGAAGCTT ACCAGACCGG TCATCAGCGC ATCGGTGCTA ACGATAACCA CATCGCCCTG    60

GGTCGGGATA AT    72

(2) INFORMATION FOR SEQ ID NO:56:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:56:

GTAAGCTTCG CGAGCCATGT GCCGTACATC GAGCAGGGTA TGCAACTGAG CGAACAATTT    60

AAGCAGAAG    69

(2) INFORMATION FOR SEQ ID NO:57:

(i) SEQUENCE CHARACTERISTICS:
      (A) LENGTH: 72 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:57:

CGGGGCGGCC GCCTCCGCCT GTTTGGTCGC GGTCTGCAGC AGACCCAGGC TCTTCTGCTT    60

AAATTGTTCG CT    72

(2) INFORMATION FOR SEQ ID NO:58:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:58:

GAGGCGGCCG CCCCGGTGGT TGGCACCCCG AAAAGCCGCC GTCCG    45

(2) INFORMATION FOR SEQ ID NO:59:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:59:

GATGGTACCC GGTTGCGCCC AGGCACGACC TTCCGGACGG CGGCTTTTC    49

(2) INFORMATION FOR SEQ ID NO:60:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:60:

CAGGGTACCA TCATCCTGAG CGGTCGTCCG GCGGTTGTAC CGGAT    45

(2) INFORMATION FOR SEQ ID NO:61:

(i) SEQUENCE CHARACTERISTICS:
      (A) LENGTH: 45 base pairs
      (B) TYPE: nucleic acid (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:61:

CTCGAGAAAT TCTTGATACA GCACTTCACG ATCCGGTACA ACCGC                45

(2) INFORMATION FOR SEQ ID NO:62:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:62:

GAGCTCGCCA TGGGCACCAA CCCGAAACCG GAGCGTAAAA GCAAGCGTAA CACCAACCGT       60

AAACCGCAGG ATATTAAA                                                    78

(2) INFORMATION FOR SEQ ID NO:63:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:63:

GCGGATCCTT ACGGACCACG ACGCGGCACC AGGTACACAC CACCCACCAC CTGACCACTA      60

CCCGGGAATT TAATATCCTG CGGTTTACG                                        89

(2) INFORMATION FOR SEQ ID NO:64:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:64:

GGCCCTGTCT AACACTGGAG AGGTCCCCTT CTATGGCCGC GCGATCCCGA T                51

(2) INFORMATION FOR SEQ ID NO:65:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:65:

GGCCCTGTCT AACACTGGAG AGGTCCCCTT CTATGGCCGC GCGATCCCGA T                51

(2) INFORMATION FOR SEQ ID NO:66:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:66:

GTTACAGTCG ACCACTGAGT CAAAATCGCC GGTAAAACCG GTCATCAGCG CATCGG      56

(2) INFORMATION FOR SEQ ID NO:67:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:67:

CGAAGCTTAC CAGTCCAGAT CCCTGGGTGA TGCATGTGTT ACAGTCGACC ACTGAGT     57

(2) INFORMATION FOR SEQ ID NO:68:

(i) SEQUENCE CHARACTERISTICS:
        (A) LENGTH: 421 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:68:

```
Met Lys Ala Ile Phe Val Leu Lys Gly Ser Leu Asp Arg Asp Pro Glu
 1               5                  10                  15

Phe Thr Lys Val Pro Ala Ala Tyr Ala Ala Gln Gly Tyr Lys Val Leu
                20                  25                  30

Val Leu Asn Pro Ser Val Ala Ala Thr Leu Gly Phe Gly Ala Tyr Met
            35                  40                  45

Ser Lys Ala His Gly Thr Asp Pro Asn Ile Arg Thr Gly Val Arg Thr
 50                  55                  60

Ile Thr Thr Gly Ala Pro Ile Thr Tyr Ser Thr Tyr Gly Lys Phe Leu
 65                  70                  75                  80

Ala Asp Gly Gly Cys Ser Gly Gly Ala Tyr Asp Ile Ile Gly Ser Gly
                85                  90                  95

Glu Glu Val Ala Leu Ser Asn Thr Gly Glu Ile Pro Phe Tyr Gly Lys
               100                 105                 110

Gly Ile Pro Ile Glu Val Ile Lys Gly Gly Arg His Leu Ile Phe Cys
           115                 120                 125

His Ser Lys Lys Lys Cys Asp Glu Leu Ala Ala Lys Leu Ser Gly Leu
130                 135                 140

Gly Ile Asn Ala Val Ala Tyr Tyr Arg Gly Leu Asp Val Ser Val Ile
145                 150                 155                 160

Pro Thr Ser Gly Asp Val Val Val Ala Thr Asp Ala Leu Met Thr
                165                 170                 175

Gly Tyr Thr Gly Asp Phe Asp Ser Val Ile Asp Cys Asn Thr Cys Val
                180                 185                 190
```

-continued

```
Thr Gln Gly Ser Gly Leu Val Ser Phe Ala Ser His Leu Pro Tyr Ile
            195                 200                 205

Glu Gln Gly Met Gln Leu Ala Glu Gln Phe Lys Gln Lys Ala Leu Gly
    210                 215                 220

Leu Leu Gln Thr Ala Thr Lys His Ala Glu Ala Ala Pro Val Val
225                 230                 235                 240

Gly Thr Pro Lys Ala Arg Arg Pro Glu Gly Arg Ala Trp Ala Gln Pro
                245                 250                 255

Gly Ser Val Val Ile Val Gly Arg Ile Ile Leu Ser Gly Arg Pro Ala
                260                 265                 270

Val Ile Pro Asp Arg Glu Val Leu Tyr Arg Glu Phe Phe Leu Glu Ala
            275                 280                 285

Ser Arg Ala Ala Leu Ile Glu Glu Gly Gln Arg Ile Ala Glu Met Leu
    290                 295                 300

Lys Ser Lys Ile Gln Gly Leu Leu Gln Gln Ala Ser Lys Gln Ala Gln
305                 310                 315                 320

Asp Ile Lys Ile Asp Gly Thr Leu Ile Ile Pro Lys Asp Arg Arg Ser
                325                 330                 335

Thr Gly Lys Ser Trp Gly Lys Pro Gly Phe Leu Ile Asp Ser Leu His
                340                 345                 350

Ile Asn Gln Arg Ala Val Val Ala Pro Asp Lys Glu Val Leu Tyr Glu
            355                 360                 365

Ala Phe Asp Glu Met Glu Leu Ala Met Gly Met Gly Thr Asn Pro Lys
    370                 375                 380

Pro Gln Arg Lys Thr Lys Arg Asn Thr Asn Arg Arg Pro Gln Asp Val
385                 390                 395                 400

Lys Phe Pro Gly Gly Gly Gln Ile Val Gly Gly Val Tyr Leu Leu Pro
                405                 410                 415

Arg Arg Gly Pro Arg
            420

(2) INFORMATION FOR SEQ ID NO:69:

(i) SEQUENCE CHARACTERISTICS:
        (A) LENGTH: 396 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:69:

Glu Phe Thr Lys Val Pro Val Ala Tyr Ala Ala Lys Gly Tyr Lys Val
1               5                   10                  15

Leu Val Leu Asp Pro Ser Val Ala Ser Thr Leu Gly Phe Gly Ala Tyr
            20                  25                  30

Leu Ser Lys Ala His Gly Val Asn Pro Asn Ile Arg Thr Gly Ile Arg
        35                  40                  45

Thr Val Thr Thr Gly Ala Pro Val Thr Tyr Ser Thr Tyr Gly Lys Tyr
    50                  55                  60

Leu Ala Asp Gly Gly Cys Ala Gly Gly Ala Tyr Asp Val Ile Gly Ser
65                  70                  75                  80

Gly Glu Glu Val Ala Leu Ser Asn Thr Gly Glu Val Pro Phe Tyr Gly
                85                  90                  95

Arg Ala Ile Pro Ile Glu Ala Ile Lys Gly Gly Arg His Leu Val Phe
            100                 105                 110
```

```
Cys His Ser Lys Glu Lys Cys Asp Glu Leu Ala Ser Ala Leu Ser Gly
        115                 120                 125

Leu Gly Leu Asn Ala Val Ala Phe Tyr Arg Gly Leu Asp Val Ser Ile
    130                 135                 140

Ile Pro Thr Gln Gly Asp Val Val Ile Val Ser Thr Asp Ala Leu Met
145                 150                 155                 160

Thr Gly Phe Thr Gly Asp Phe Asp Ser Val Val Asp Cys Asn Thr Cys
                165                 170                 175

Ile Thr Gln Gly Ser Gly Leu Val Ser Phe Ala Ser His Val Pro Tyr
            180                 185                 190

Ile Glu Gln Gly Met Gln Leu Ser Glu Gln Phe Lys Gln Lys Ser Leu
        195                 200                 205

Gly Leu Leu Gln Thr Ala Thr Lys Gln Ala Glu Ala Ala Pro Val
    210                 215                 220

Val Gly Thr Pro Lys Ser Arg Arg Pro Glu Gly Arg Ala Trp Ala Gln
225                 230                 235                 240

Pro Gly Thr Ile Ile Leu Ser Gly Arg Pro Ala Val Val Pro Asp Arg
                245                 250                 255

Glu Val Leu Tyr Gln Glu Phe Leu Glu Ala Ser Arg Ala Ala Leu Ile
            260                 265                 270

Glu Glu Gly Gln Arg Ile Ala Glu Met Leu Lys Ser Lys Ile Gln Gly
        275                 280                 285

Leu Leu Gln Gln Ala Ser Lys Gln Ala Gln Asp Ile Lys Ile Asp Gly
    290                 295                 300

Thr Leu Ile Ile Pro Lys Asp Arg Arg Ser Thr Gly Lys Ser Trp Gly
305                 310                 315                 320

Lys Pro Gly Phe Leu Ile Asp Ser Leu His Ile Asn Gln Arg Ala Val
                325                 330                 335

Val Ala Pro Asp Lys Glu Val Leu Tyr Glu Ala Phe Asp Glu Met Glu
            340                 345                 350

Leu Ala Met Gly Thr Asn Pro Lys Pro Glu Arg Lys Ser Lys Arg Asn
        355                 360                 365

Thr Asn Arg Lys Pro Gln Asp Ile Lys Phe Pro Gly Ser Gly Gln Val
370                 375                 380

Val Gly Gly Val Tyr Leu Val Pro Arg Arg Gly Pro
385                 390                 395

(2) INFORMATION FOR SEQ ID NO:70:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

Arg Arg Gln Pro Ile Pro Lys Ala Arg Arg Pro Glu Gly Arg Thr Trp
1               5                   10                  15

Ala Gln Pro Gly
            20

(2) INFORMATION FOR SEQ ID NO:71:

(i) SEQUENCE CHARACTERISTICS:
        (A) LENGTH: 20 amino acids
```

-continued

```
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

Arg Arg Gln Pro Ile Pro Lys Ala Arg Gln Pro Glu Gly Arg Ala Trp
1               5                   10                  15

Ala Gln Pro Gly
            20

(2) INFORMATION FOR SEQ ID NO:72:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

Arg Arg Gln Pro Ile Pro Lys Asp Arg Arg Ser Thr Gly Lys Ser Trp
1               5                   10                  15

Gly Lys Pro Gly
            20
```

CHIMERA ANTIGEN PEPTIDE

BACKGROUND OF INVENTION

1. Field of Invention

The present invention relates to an antigen peptide which is capable of detecting a wide range of infection by hepatitis C virus (HCV).

2. Related Art

Non-A, non-B hepatitis is an infectious hepatitis which is believed to be transmitted by means of virus as an agent. Although much remains to be known about the transmission route of non-A, non-B hepatitis, transfusion- or blood products-derived non-A, non-B hepatitis represents a serious medical problem as post-transfusion hepatitis.

In 1989 part of the viral gene associated with non-A, non-B hepatitis was cloned and was designated as hepatitis C virus (HCV) (1989, Choo Q. -L. et al., Science 244: 359–362). At about the same time many HCV genes were isolated by many research groups including the applicant of the present invention, leading to the elucidation of structural features thereof.

The deduced HCV gene has a+strand RNA composed of about 9,300 to 9,500 nucleotides as the genome and encodes one stretch of polypeptide having about 3,000 amino acids. The predicted amino acid sequence thereof has a homology with flavivirus or pestivirus and, thereby HCV virus is believed to be an allied virus thereof. From its similarity to the structures of these viruses, it is believed that the polypeptide encoded by the HCV genome, after being synthesized as a single polypeptide in the cell, is cleaved from the amino-terminal into the structural proteins, core, envelope (E1), and NS1 or E2 (NS1/E2), and the non-structural proteins, NS2, NS3, NS4, and NS5, and then each plays its respective role (1991, Houghton, M. et al., Hepatology 14: 381–391).

Conventional methods used to investigate HCV infection involve the use of these polypeptides encoded by the HCV genome to detect antibodies induced within the patient's body. In particular, since antibodies against core, NS3, and NS4 have been found in many patients with HCV, reagents for detecting antigen-antibody reactions have been prepared using as the antigen part of these polypeptides which were produced by means of genetic engineering, and have played a role in identifying the presence of HCV infection.

However, there is no known antigen which is a single polypeptide comprising a combination of epitope peptides alone and which permits a sensitive detection of a wide range of HCV infection.

SUMMARY OF THE INVENTION

The present invention provides an antigen peptide which permits sensitive detection of a wide range of hepatitis C virus (HCV)infection, a method of producing said antigen, and a method of detecting HCV infection using said antigen peptide.

In order to solve the above problems, the present invention provides a chimera antigen peptide against an HCV antibody comprising a polypeptide wherein at least two or more peptide regions from each of the core region, the NS3 region, and the NS4 region of the HCV polypeptide have been joined.

Thus, the present invention provides an HCV chimera antigen peptide comprising at least two epitope peptide regions of the core region, two epitope peptide regions of the NS3 region, and at least two epitope peptide regions of the NS4 region of the HCV polypeptide. The HCV chimera antigen peptide of the present invention specifically binds to antibodies produced by humans.

More specifically, the present invention provides a chimera antigen peptide comprising three polypeptide regions (C-1, CI, and CII) contained in the core region, two amino acid regions (NS3-1 and NS3-2) contained in the NS3 region, and four amino acid regions (NS4-I1, NS4-I2, NS4-II1, and NS4-II2) contained in the NS4 region of the HCV polypeptide provided that CI, NS4-I1, and NS4-I2 are derived from type I HCV, and CII, NS4-II1 and NS4-II2 are derived from type II HCV. The present invention also provides a chimera antigen peptide which has an amino acid sequence having a homology of 80% or more with the above amino acid sequence.

Preferably the present invention provides a chimera antigen peptide wherein C-1 comprises the amino acid sequence 1–43 (SEQ ID NO: 36) of the HCV polypeptide, CI comprises the amino acid sequence 66–80 (SEQ ID NO: 37) of the type I HCV polypeptide, CII comprises the amino acid sequence 66–80 (SEQ ID NO: 38) of the type II HCV polypeptide, NS3-1 comprises the amino acid sequence 1238–1313 (SEQ ID NO: 39) of the HCV polypeptide, NS3-2 comprises the amino acid sequence 1363–1460 (SEQ ID NO: 40) of the HCV polypeptide, NS4-I1 comprises the amino acid sequence 1712–1750 (SEQ ID NO: 41) of the type I HCV polypeptide, NS4-I2 comprises the amino acid sequence 1678–1705 (SEQ ID NO: 42) of the type I HCV polypeptide, NS4-II1 comprises the amino acid sequence 1716–1750 (SEQ ID NO: 43) of the type II HCV polypeptide, and NS4-II2 comprises the amino acid sequence 1690–1713 (SEQ ID NO: 44) of the type II HCV polypeptide. The present invention also provides a chimera antigen peptide which has an amino acid sequence having a homology of 80% or more with the above amino acid sequence.

More specifically, the present invention provides an HCV chimera antigen peptide which comprises: a single polypeptide comprising the peptide region from position 1238 to position 1311 or from position 1238 to position 1313, the peptide region from position 1363 to position 1460, the peptide region from position 1712 to position 1751, the peptide region from position 66 to position 80, and the peptide region from position 1686 to position 1704 of the HCV polypeptide belonging to the genotype group 1; the peptide region from position 1716 to position 1751, the peptide region from position 66 to position 80, and the peptide region from position 1690 to position 1714 of the HCV polypeptide belonging to the genotype group 2; and, the peptide region from position 1 to position 43 or from position 1 to position 42 of the HCV polypeptide belonging to the genotype group 1 or 2, wherein the above regions may be joined by a linker peptide having no epitope activity; or a single polypeptide which has an amino acid sequence having a homology of 80% or more with the above amino acid sequence.

The present invention also provides DNA encoding the above chimera antigen peptide.

Furthermore, the present invention provides a vector, particularly an expression vector, comprising the above DNA.

The present invention also provides a host which has been transformed by the above expression vector.

Furthermore, the present invention provides a method of producing a chimera antigen peptide comprising culturing the above host, and harvesting said chimera antigen peptide from said culture.

The present invention also provides a method of detecting HCV infection comprising contacting a test sample with the above chimera antigen peptide, and determining whether an antigen-antibody reaction has taken place between them.

In accordance with the technology illustrated by the present invention, the non-specific reactions between antigen and antibody, which always provide problems in the methods employing antigen-antibody reactions, can be reduced, the reactivity of specific reactions between antigens and antibody can be enhanced, and enhanced function of a peptide antigen can be applied to immunological diagnostic methods employing antigen-antibody reactions.

Furthermore, the use of a polypeptide illustrated by the present invention enables detection of antibody to HCV in the serum of patients with HCV infection and thereby is useful for correct identification of the presence of HCV infection.

In accordance with the present invention, the performance, which could only be attained by the production of multiple antigens in the conventional methods, can be attained by the use of one antigen. This has led to a higher efficiency in production such as reduced number of production steps, simplified methods of production, and reduced numbers of tests and simplified testing related to production such as quality control as compared to the conventional methods.

DETAILED DESCRIPTION

Since part of the gene fragment encoding the information required for HCV to propagate was isolated prior to the discovery of HCV itself, diagnosis of HCV infection relied on a diagnostic method which employs an expression product of the above isolate by recombinant gene technology using yeast as the host. It has been reported that this so-called first generation reagent (1989, Kuo, G. et al., Science 244: 362–364) which uses the C100-3 antigen enabled detection of about 70% of the patients with HCV infection.

However, subsequent studies revealed that the C100-3 antibody has a high rate of false positive and it has been reported that at present the elimination of the C100-3 antibody led to a more definite identification of infection (1994, Zaaijer, H. L. et al., Vox Sang. 66: 150).

Generally, as a method for enhancing the ratio of the specific/non-specific reactions there has been used a method in which the number of epitopes which cause specific reactions are increased so that the relative ratio of the specific/non-specific reactions is increased. This method has also been used in the development of diagnostic reagents for HCV infection, with a result, for example, that when the first generation reagent was replaced by the second generation reagent, recombinant antigens of the core region and the NS3 region were added to C100-3, which enabled detection the antibody in the patients which could not be detected by C100-3 alone.

At this time there was also a decline in the sensitivity of C100-3, which resulted in reduced non-specific reactions (1992, Shiro Iino and Kunihiko Hino, Taisha (Taisha) 29: 503–511; 1993, Norio Hayashi et al., Nippon Rinsho 51:329–333). This was not caused by decreased non-specific reactions which generate false positive reactions of C100-3, but by the addition of the regions (the core region, the NS3 region) which generate specific reactions with a relative decline of C100-3 reactivity and a resultant increase in the specific/non-specific reaction ratio. This allowed more reliable identification results to be obtained. However, there are still many problems reported even when using these improved reagents for detection.

There are reports, for example, that even the latest, so-called the third generation assay kit does not give positive results for some of the patients infected with HCV (1994, B. C. Dow et al., Vox Sang. 67: 236–237), and that HCV infection has been supported by PCR in many of the indeterminate samples by the third generation assay kit (1994, L. Dussaix et al., J. Clin. Microbiol. 32: 2071–2075). Further improvements are thereby desired.

The present invention intends to increase the specific/non-specific reaction ratio and thus to enhance reliability of the identification results using the methods different from the conventional ones.

Thus, the present invention is constructed by determining whether an antigen, when reacted with a patient serum, is bound by a specific and clinically important antibody-binding sequence (epitope) or by a non-specific reaction, selecting the sequence only that generates a clinically important specific reaction, and constructing an antigen composed of an artificial gene sequence that is devoid of the sequence which was found to induce non-specific reactions.

In accomplishing the present invention, the sequences that are necessary and sufficient to detect anti-HCV antibody from among the HCV polypeptides were investigated. For such investigation, the core region (C11 antigen: 1992, M. Saito et al., Clin. Chem. 38: 2434–2439), the NS3 region (C7 antigen: 1992, M. Saito et al., Clin. Chem. 38: 2434–2439), and the NS4 region (C14-1, C14-2: 1994, T. Tanaka et al., Hepatol. 19: 1347–1353) were used. The NS5 region was seemed to be unworthy of investigation since there were many reports to the effect that "The reaction is considered to be false positive, since there are few patient sera that react with the NS5 region and very few sera that react with the NS5 antigen alone, and these turn out to be negative by PCR which detect the presence of HCV" (1994, Lancet 343: 853–854; 1994, S. Uyttendaele et al., Vox Sang. 66: 122–129).

In order to accomplish the present invention, the necessary and sufficient sequences were further classified into the necessary sequences and the unnecessary sequences which cause non-specific reactions. The epitopes present in polypeptide antigens include those composed of relatively short stretches of contiguous amino acids and those resulting from assembling the amino acid residues which are distant on the primary structure into higher structures (Menekigaku Jiten (Dictionary of Immunology), Tokyo Kagaku Dojin, 1993).

A representative method for determining an epitope includes the PEPSCAN method developed by Geysen et al. (1987, Geysen et al., J. Immunol. Meth. 102: 259–274). This method is suitable for determining epitopes composed of relatively short stretches of contiguous amino acid sequence since relatively short (6 to 7 amino acid long) peptide chains synthesized on a solid phase react with the antibody. However, in this method is it difficult to detect epitopes comprising a higher structure constructed by amino acid residues which are distant on the primary structure. Thus, epitope analysis is preferably conducted using relatively long strands of amino acid sequence (polypeptides of 20 to 60 amino acids) that were synthesized chemically or by genetic engineering for analysis of epitopes.

Epitome Analysis of the Core Region

For the polypeptide of at positions 1 to 160 of the HCV polypeptide, 20 amino acids-long peptides comprising 10 amino acids such as 1 to 20, 11 to 30, 21 to 40 were chemically synthesized. Investigation of reactivity of them with patient sera revealed that most of the peptides which reacted strongly with patient sera belong to those from 1 to 40 and that they are epitopes which exhibit strong antigenicity.

On the other hand, as has already been demonstrated by the present applicant, in the core region of the HCV polypeptide there is a region having a different reactivity due to infection of HCV group 1, 2 (Japanese Unexamined Patent Publication (Kokai) No. 6-232073). The region falls under the region from 61 to 80. For this region Group I and II were compared and the results are shown below.

TABLE 1

```
                70             80
Group I   RRQPIPKARR PEGRTWAQPG (SEQ ID NO:70)
          |||||||||| ||||||||||
          RRQPIPKARR PEGRTWAQPG (SEQ ID NO:70)
          |||||||||| |||| ||||| 
          RRQPIPKARq PEGRaWAQPG (SEQ ID NO:71)
          ||||||| |   |  |  ||
Group II  RRQPIPKdRR stGksWgkPG (SEQ ID NO:72)
          |||||||||| ||||||||||
          RRQPIPKdRR stGksWgkPG (SEQ ID NO:72)
```

It is clear that in the above region the amino acid sequences have been conserved among the groups whereas the amino acid sequences are different among the groups. Whether the sequences in this region have antigenicity and can be used as the antigen for identifying the groups may be demonstrated by preparing peptides having respective amino acid sequences and by determining their reactivity with patient sera.

Example 1 shows the results obtained. Since a smaller number of sera reacted with the peptides compared with when the NS4 region is used, they do not seem to provide major epitopes for identifying the groups. However, by the method for identification using PCR and the NS4 region it was shown that they react specifically with each of the HCV groups. A more detailed examination revealed that there are some patient sera in Group I which do not react with the NS4 region but with only this region in a group-specific manner.

Similar results to the one described above have been demonstrated by Machida et al. (Machida et al., Hepatology (1992) 16: 886–891) using a peptide having the sequence in the region 65 to 81.

It was revealed from the foregoing that the epitope sequences necessary for diagnosis of HCV in the core region are the sequence from position 1 to position 40, the sequence from position 65 to position 80 of Group 1 HCV, and the sequence from position 65 to position 80 of Group 2 HCV.

Epitope Analysis of the NS3 Region

Antibodies which react with part of the NS3 region, a polypeptide comprising 1221 to 1473 of the HCV polypeptide, are found in many patient sera and the region exhibits strong antigenicity (Japanese Patent Application No. 2-339589). In order to limit the sequences important for specific reactions, the peptides having the sequence from 1221 to 1282 C7-1), from 1265 to 1330 C7-2), from 1308 to 1371 C7-3), from 1340 to 1409 C7-4), from 1388 to 1443 C7-5), and from 1409 to 1473 C7-6) were produced by the gene recombinant technology and were evaluated for reactivity with antibodies in the patient serum.

As a result, C7-2, C7-5, and C7-6 reacted with many patient sera. However, out of the sera that reacted with the entire antigen (1221 to 1473), only about 60% of the sera reacted with any of C7-1 to C7-6 indicating that there are epitopes of which reactivity disappears despite the fact that the recombinant antigen used was a relatively long strand, i.e. the strong structural epitopes assembled from amino acids which are distant from one another on the primary structure. On the other hand, though C7-3 reacted well with the patient sera it reacted with many of the sera of normal subjects, thereby showing that this region has sequences that cause non-specific reactions.

Then a study was conducted to locate the region that produces such a higher structure-dependent epitope. A relatively long polypeptide, C7-46, comprising 1340 to 1473 of the HCV polypeptide was prepared to evaluate its reactivity with patient sera. This relatively long stranded peptide reacted with many of patient sera. The sera which reacted comprised those that reacted with either of C7-4, C7-5, and C7-6, and those that did not react with any of these but with the long stranded C7-46.

From the foregoing, it was shown that by making a long chain of C7-46 a higher structure-dependent epitope was constituted thus leading to enhanced reactivity. The reactivity of C7-46 was also retained in a further shortened C7-Native.

These results revealed that as the epitope regions of the NS3 region the sequence from position 1238 to position 1311 which includes C7-2 and part of C7-46, i.e. the sequence from position 1366 to position 1460, are necessary and sufficient for detecting anti-HCV NSB antibody.

Epitope Analysis of the NS4 Region Peptides

The C14-1-2 antigen and the C14-2-2 antigen encoding part of the ND4 region react with the antibodies in the patient sera infected with Group 1 and Group 2, respectively, of HCV (Japanese Patent Application No. 5-194185). The C100-3 antigen comprising the NS4 region and the 5-1-1 antigen comprising part of the C100-3 antigen which have been conventionally used for identifying HCV infection exhibit a similar reactivity to that of the C14-1-2 antigen. Thus, the conventionally used C100-3 antigen and the 5-1-1 antigen comprising part of the C100-3 antigen react well with the patient serum infected with Group 1 but react poorly with the patient serum infected with Group 2.

Therefore, in order to detect the presence of HCV infection using the NS4 region, the antigen must show a reactivity in any of the HCV infections of Group 1 and 2. Thus, the applicant has combined the epitopes of the C14-1-2 and the C14-2-2 antigens and succeeded in enhancing the function of the antigens currently in use. The inventor thereby decided to employ the combined antigen polypeptide as part of the antigen for optimum detection of HCV antibody.

The epitopes present on these polypeptides were determined by the inhibition test using the peptides. In a specific method shown in Example 2, the reaction of the C14-1-2 antigen with antibodies in the patient sera was inhibited by adding the peptides 1-W, 1-X, and 1-Y into the reaction. For the sera for which inhibition was observed by the addition of 1-W, the inhibition of the reaction was observed by the addition of 1-Wa which has the fragmented sequences of the 1-W sequence.

On the other hand, the reaction of the C14-2-2 antigen with antibodies in the patient sera was inhibited by adding the peptides 2-W, 2-X, and 2-Y into the reaction. For the sera for which inhibition was observed by the addition of 2-W, the inhibition of the reaction was observed by the addition of 2-Wa which has the fragmented sequences of the 2-W sequence.

These results demonstrated that the antibody epitope present on the antibody in the serum of patients infected with the Group 1 HCV is located on the sequence from position 1712 to position 1750 and the sequence from position 1678 to position 1705 of the polypeptide sequence of the Group 1 HCV, whereas the antibody in the serum of patients infected with the Group 2 HCV is located on the sequence from position 1716 to position 1750 and the sequence from position 1690 to position 1713 of the polypeptide sequence of the Group 2 HCV.

Designing the Epitope-chimera Antigen

The epitope-chimera antigen which was made possible by the present invention cannot be produced by merely combining the elucidated antigens. When the epitope sequences are merely combined, the sequence resulting from the binding of the epitopes creates new epitopes, which may cause non-specific reactions.

When the peptide is a short chain, as was shown in the epitope analysis of the NS3 region, it may not function as an epitope. When the chain length of the peptide is lengthened to avoid this, such an epitope which could not be found in the short chain may function as an epitope, thus exhibiting a function other than was desired.

The present invention also provides methods for solving problems as above.

Epitope-chimera antigens can be efficiently designed in accordance with the following procedure. First, it is important to examine the property of the epitope peptide. That is, an epitope binds non-covalently to the biding site (paratope) of the antibody to which the epitope is to be bound via hydrogen bonding, ionic bonding, van-der Waals force, hydrophobic bonding etc. For a binding to be formed a fixed three-dimensional configuration must be formed between the site on the epitope to which these forces act and the site on the paratope to which the forces act.

Thus, in order for the peptide, comprising the sequences which should function as the epitope, to function as the epitope, it is necessary to make a three-dimensional structure that permits binding to the paratope. On the other hand, since a higher structure of a peptide changes due to changes in the length of the peptide and the addition of amino acids to the peptide, the mere addition of the epitope-peptide may cause a loss of antigenicity. Accordingly, in designing an epitope-chimera antigen it is necessary to employ a method for enhancing the reactivity with the serum of HCV patients who test positive for the antibody by introducing the epitope-peptide to the epitope-chimera antigen. For this purpose information is necessary on the original structure of the epitope-peptide to be combined.

In order to know the structure of an epitope-peptide, the structure elucidated by, where available, X-ray analysis and nuclear magnetic resonance (NMR) analysis of the crystal structure may be used. However, since this is not common, analysis is performed by the method of predicting a secondary structure from the amino acid sequence of the peptide, for example, using a calculation formula developed by Chou and Fasman et al. (Chou P. Y. & Fasman G .D., (1974) Biochemistry 13: 211–222; Chou P. Y. & Fasman G. D., (1974) Biochemistry 13:222–245; Chou P. Y. & Fasman G. D. (1978) Ann. Rev. Biochem. 47: 251–276) or the calculating formula developed by Robson et al. (Robson B. & Suzuki E., (1976) J. Mol. Biol. 107: 327–356; Garnier, J., Osguthorpe D. J. & Robson B., (1978) J. Mol. Biol. 120: 97–120) and the like.

Furthermore, it is preferred to obtain in advance the information on the property exhibited by the epitope-peptide by conducting the hydrophobicity-hydrophilicity plot of protein according to the calculating formula developed by Hopp and Woods (Hopp T. P. & Woods K. R., (1981) Proc. Natl. Acad. Sci. U.S.A. 78: 3824–3828) and Kyte and Doolittle (Kyte J. & Doolittle R. F., (1982) J. Mol. Biol. 157: 105–132). Furthermore, it is also preferred to understand the predicted property based on the antigenicity of the desired peptide according to the calculating formula proposed by Jameson and Wolf (Jameson B. A. & Wolf H., (1988) Comput. Applic. in Biosciences 4: 181–186).

Furthermore, the information obtained by the method of predicting the surface site proposed by Janin et al. and Emini et al. (Jamin J., Wodak S., Levitt M. & Maigret B., (1978) J. Mol. Biol. 125: 357–386; Emini E., Hughes J. V., Perlow D.S., & Boger J., (1965) J. Biol. 55: 836–839) and the method of predicting the plasticity of protein proposed by Karplus et al. (Karplus P. A. & Schulz G.E., (1985) Naturwiss. 72: 212–213) is also useful for predicting antigenicity.

In designing an epitope-chimera antigen, care should be taken to enhance the reactivity with the serum of antibody-positive patients with HCV by introducing the epitope-peptide to be combined, and to link a linker-peptide which does not show any reactivity with the serum of normal subjects by combination, using the above-mentioned prediction methods as a reference.

In order to complete the epitope-chimera antigen of the present invention, it is not sufficient to design a gene based on the above-mentioned prediction methods. It is also necessary to express the gene, to confirm the reactivity with the serum of antibody-positive patients with HCV, and furthermore to confirm the absence of non-specific reactions using the sera of a number of normal subjects.

By designing based on the above design policy in which the functions of the antigens with different alignments that were expressed in *E. coli* and purified was confirmed, by the above method for confirming the function, an epitope-chimera antigen comprising the amino acid sequence starting with the amino acid Thr at position 18 out of the amino acid sequence as set forth in SEQ ID NO: 1 was completed.

In this antigen the epitope fragments have been bound in the alignment (1238–1313 ; Group 1)—(1363–1460; Group 1)—(1712–1750; Group 1)—(66–80; Group 1)—(1678–1705; Group 1)—(1716–1750; Group 2)—(66–80; Group 2)—(1690–1713; Group 2)—(1–43). Though this sequence is one of the preferred embodiments of the antigen alignment, other alignments are also possible in accordance with the above design policy and the method for confirmation.

For example, the antigen comprising the epitope fragment (1238–1313 ; Group 1-like)—(1363–1460; Group 1-like)—(1712–1751; Group 1-like)—(66–80; Group 1-like)—(1686–1704; Group 1-like)—(1716–1751; Group 2)—(66–80; Group 2)—(1690–1713; Group 2)—(1–42; Group 1-like) is illustrated as a sequence of a preferred embodiment. "Group 1-like" as used herein means an amino acid sequence having a high homology with the amino acid sequence of the corresponding region in Group 1.

An example of the entire amino acid sequence of a chimera antigen peptide designed based on the above policy is shown in SEQ ID NO: 47. In the sequence, the amino acid sequence starting with the amino acid Thr at position 3 represents the amino acid sequence of the chimera antigen peptide.

It has been confirmed that both of the polypeptide having the amino acid sequence as set forth in SEQ ID NO: 1 and the polypeptide having the amino acid sequence as set forth in SEQ ID NO: 47 have the antigenicity of the present invention. The amino acid sequence of SEQ ID NO: 1 and that of SEQ ID NO: 47 have a homology of about 80%. Thus, the antigen peptide which has a homology of 80% or greater with the amino acid sequence as set forth in SEQ ID NO: 1 and which specifically binds to the antibody produced by humans infected with HCV is encompassed in the present invention.

Construction of an Epitope-chimera Antigen

The epitope-chimera antigen designed by the above-mentioned method can be constructed by chemical synthesis based on various principles and also by genetic engineering technology as well.

The genetic engineering technology involves a step of isolating a DNA fragment encoding a peptide having at least an amino acid sequence starting with the amino acid Thr at position 18 out of the amino acid sequence as set forth in SEQ ID NO: 1 or an amino acid sequence starting with the amino acid Thr at position 3 out of the amino acid sequence as set forth in SEQ ID NO: 47 or a partial sequence thereof from the HCV genomic RNA or cDNA thereof by a method commonly used in the art, or a chemical synthetic step, and the step obtained by combining these technologies.

There are also included a step of constructing an expression vector capable of replication containing a DNA fragment encoding the above peptide, a step of introducing said expression vector into a host cell and obtaining a transformant which expresses said peptide, a step of culturing said transformant to express an expression product, and a step of recovering the expressed peptide.

For example, the DNA fragment encoding a peptide having an amino acid sequence starting with the amino acid Thr at position 18 out of the amino acid sequence as set forth in SEQ ID NO: 1 or an amino acid sequence starting with the amino acid Thr at position 3 out of the amino acid sequence as set forth in SEQ ID NO: 47 or a partial sequence thereof can be produced as shown in Example 4 or 7. It is also possible to obtain a transformant as shown in Example 5 or 7, to culture the transformant as shown in Example 5 and 8, and to separate and recover said peptide.

Expression vectors for use in the genetic engineering technology may include, in addition to a vector which permits expression under the control of E. coli tryptophan operon using E. coli as the host as is disclosed in the Examples, vectors which utilize Tac promoter, Trc promoter, lac promoter, PhoA promoter, lac promoter and the like in addition to E. coli tryptophan operon using E. coli as the host.

Using yeast in place of E. coli, it is also possible to conduct expression using an expression vector which utilizes a promoter commonly used for yeast such as glycolysis genes including glyceraldehyde-3-phosphate dehydrogenase, alcohol dehydrogenase I and II, pyruvate kinase, phosphoglycerin kinase, triose isomerase etc. Furthermore, it is also possible to conduct expression by an expression system using baculovirus as the vector with an insect cell as the host, an expression system in which a mammalian cell such as a CHO cell, a COS cell, etc. is used as the host and a conventionally used integrated expression vector or vaccinia virus is used as the vector, and an expression system in which adenovirus or a conventionally used virus is used as the vector.

Furthermore, when the genetic engineering technology is used, the expression of a chimera antigen peptide as a fusion protein with another peptide is a conventionally used means.

The chimera antigen thus produced is capable of detecting anti-HCV antibody in the serum of HCV patients as shown in Example 6 and 9.

EXAMPLES

Although a more detailed explanation will be given hereinbelow, it should be apparent from the foregoing that it will not limit the present invention in any way.

Example 1

Epitope Analysis of the Core Region

A peptide having the sequences as set forth in SEQ ID NO: 2 or 3 was synthesized using the peptide synthesizer (Model: 430A) of Applied Biosystems and was subjected to a reverse-phase chromatography to purify the desired peptide. The similarity of the purified peptide with the desired peptide was confirmed by analyzing with an amino acid sequencer.

The peptide was diluted in 0.1 M phosphate buffer, pH 7.5, containing 8 M urea to a concentration of 2.5 $\mu$g/ml. The diluted antigen was applied to a multi-module Nunc plate at an amount of 100 $\mu$l per well and was allowed to stand for 2 hours at room temperature. After removing the antigen dilution solution, 100 $\mu$l per well of the blocking solution (0.5% casein, 0.15 M NaCl, 2.5 mM EDTA, 0.1 M phosphate buffer, pH 7.0) was added and allowed to stand for 2 hours at room temperature to immobilize the antigen on the plate.

To each well was added 100 $\mu$l each of the sera of patients with non-A, non-B hepatitis diluted 11-fold with the sample dilution buffer (0.5% casein, 0.5 M NaCl, 2.5 mM EDTA, 0.1 M phosphate buffer, pH 7.0), which were then allowed to stand for 45 minutes. After the wells were washed in PBS containing 0.1% Tween 20, 100 $\mu$l of horseradish peroxidase-labelled anti-human IgG antibody was added thereto and were allowed to stand for 45 minutes. After the wells were washed in PBS containing 0.1% Tween 20, enzymatic activity was determined by the color development method according to the conventional method. The results are summarized in Table 2.

TABLE 2

| | PCR | ELISA core | |
|---|---|---|---|
| Sample No. | Group | sequence 1 | sequence 2 |
| 2 | II | 0.048 | 2.923* |
| 3 | I | 2.209* | 0.035 |
| 4 | I | 0.005 | 0.027 |
| 5 | II | 0.018 | 0.036 |
| 6 | II | 0.253 | 0.250 |
| 7 | I | 2.885* | 0.028 |
| 9 | I | 0.249 | 0.025 |
| 10 | — | 0.153 | 0.025 |
| 11 | I | 0.005 | 0.023 |
| 12 | I | 2.923* | 0.026 |
| 14 | I | 0.061 | 0.025 |
| 15 | I | 0.024 | 0.017 |
| 16 | I | 2.926* | 0.027 |

TABLE 2-continued

| | PCR | ELISA core | |
|---|---|---|---|
| Sample No. | Group | sequence 1 | sequence 2 |
| 17 | II | 0.003 | 0.047 |
| 18 | II | 0.002 | 0.027 |

Note: In the PCR column the result of the group identified by the PCR method is shown, in which Group I is indicated as I and Group II is indicated as II in the table. — indicates the case which could not be identified by the PCR method. On the other hand the ELISA column shows a reading at OD492 obtained by the color development method. High values have been marked with *.

The result confirmed that the amino acid sequences as set forth in SEQ ID NO: 2 and 3 correspond to the type I HCV polypeptide and the type II HCV polypeptide, respectively.

Example 2

Epitope Analysis of the NS3 region

In order to obtain fragments having a partial sequence of the NS3 region, the 12 primer DNAs shown in Table 3 were synthesized using the DNA synthesizer (ABI, Model 394A or Milligen/Biosearch, Model 8700).

TABLE 3

The nucleotide sequence of primers

| | Sequence | |
|---|---|---|
| 1F | GCGAATTCCAGTCATTCCAAGTGGCCCAT | (SEQ ID NO: 4) |
| 1R | CAGGATCCTTACCCAGTTCTGATGTTGGG | (SEQ ID NO: 5) |
| 2F | GCGAATTCGGAGCGTATATGTCTAAG | (SEQ ID NO: 6) |
| 2R | CAGGATCCTTAGCCGATGCCCAAGATGGA | (SEQ ID NO: 7) |
| 3F | GCGAATTCGGCGCTTATGACATCATA | (SEQ ID NO: 8) |
| 3R | CAGGATCCTTATCCAGTGTTAGACAGGGC | (SEQ ID NO: 9) |
| 4F | GCGAATTCGGAGCACGGCTCGTCGTG | (SEQ ID NO: 10) |
| 4R | CAGGATCCTTATGACAACTTCGCGGCGAG | (SEQ ID NO: 11) |
| 5F | GCGAATTCGGAAGGCATCTCATTTTC | (SEQ ID NO: 12) |
| 5R | CAGGATCCTTAGCCCGTCATATGAGCGTC | (SEQ ID NO: 13) |
| 6F | GCGAATTCGGCCTCGGGATTAATGCT | (SEQ ID NO: 14) |
| 6R | CAGGATCCTTACTCAATGGTGAAGGTGGG | (SEQ ID NO: 15) |

Using 1 ng of p3N2, a DNA containing the NS3 region (Japanese Unexamined Patent Publication (Kokai) No. 5-84, 085), PCR (polymerase chain reaction) was conducted using 100 pmol each of the combination of primers 1F and 1R, 2F and 2R, 3F and 3R, 4F and 4R, SF and 5R, or 6F and 6R. As a result a fragment (the C7-1 fragment) encoding the region corresponding to the HCV polypeptide 1221 to 1281 was obtained from 1F and 1R, a fragment (the C7-2 fragment) encoding the region corresponding to the HCV polypeptide 1265 to 1330 was obtained from 2F and 2R, a fragment (the C7-3 fragment) encoding the region corresponding to the HCV polypeptide 1308 to 1371 was obtained from 3F and 3R, a fragment (the C7-4 fragment) encoding the region corresponding to the HCV polypeptide 1340 to 1409 was obtained from 4F and 4R, a fragment (the C7-5 fragment) encoding the region corresponding to the HCV polypeptide 1388 to 1443 was obtained from 5F and 5R, a fragment (the C7-6 fragment) encoding the region corresponding to the HCV polypeptide 1409 to 1473 was obtained from 6F and 6R, and fragment C7-46 corresponding to the HCV polypeptide 1340 to 1473 was obtained from 4F and 6R.

The amplified DNA fragment was separated on 2% agarose gel electrophoresis and was recovered from the agarose gel using the MERMAID nucleic acid purification Kit (Bio101). The recovered fragment was cloned into pGEM-T (Promega) and its nucleotide sequence was determined by analysis using the DNA sequencer (ABI: Model 373A) with the Dye terminator cycle sequencing kit (ABI) to confirm that the desired fragment has been cloned.

The plasmid DNA of which fragment was cloned was cleaved with EcoRI and BamHI, was separated on 2% agarose gel electrophoresis, and each of the C7-1 to C7-6 fragments were recovered using the MERMAID nucleic acid purification Kit (Bio101). The recovered fragment was cloned into a vector ptrcTrpE for expression as a fusion protein with TrpE using trc promoter to obtain pC7-1, pC7-2, pC7-3, pC7-4, pC7-5, and pC7-6. From C7-46, pC7-46 was obtained by cloning the fragment recovered using the MERMAID nucleic acid purification Kit (Bio 101) into pAT-TrpE. Transformants of E. coli strain 10 (Invitrogen), transformed by these plasmids, were used to express recombinant antigens.

For C7-1 through C7-6 the recombinant antigen was expressed by incubating the transformant under shaking at 37° C. in the LB medium containing ampicillin to an OD600 of 0.5, to which was added IPTG (isopropyl-β-D-thiogalacto-pyranoside) to a final concentration of 0.4 mM and further incubated under shaking at 37° C. for 4 hours.

The antigen was purified by harvesting the cell mass, suspending one gram of the mass in 5 ml of the cell lysis buffer (50 mM Tris-HC1, pH 8.5, 30 mM NaCl, 5 mM EDTA, 200 µg/ml lysozyme), incubating it at 37° C. to dissolve the cell wall, and then disrupting it by sonication to obtain an insoluble fraction, from which said antigen was purified. Each antigen except for C7-6 could be extracted with the buffer (50 mM Tris-HCl, pH 8.0) to which 4 M or 6 M urea had been added, and for C7-6 the 4 M guanidine hydrochloride-added buffer was used for extraction thereof.

C7-1 was purified from the extract using cation exchange chromatography, C7-2 was purified from the extract using anion exchange chromatography and reverse-phase chromatography, C7-3 was purified from the extract using anion exchange chromatography and gel filtration chromatography, C7-4 was purified from the extract using reverse-phase chromatography, C7-5 and C7-6 were purified from the extract using anion exchange chromatography.

C7N was constructed as follows. The oligonucleotide primers were synthesized by the phospharamidite method using the Cyclone Plus DNA synthesizer (MILLIPORE) according to the manufacturer's protocol. The sequences of the synthesized oligonucleotide primers are shown below:

C7S2: 5'-GGAAMTTCGAGGAGGTGGCCCTG TCTAACACT-3' (SEQ ID NO: 45),

C7AS2: 5'-GGGATCCTTACTGGGTGACGCATGT GTTACAGTC-3' (SEQ ID NO: 46).

Using the above primers the fragments for expression of C7N were obtained by PCR and cloned into a vector, and then the sequences were confirmed.

First, 1 µl (1 ng) of plasmid C11-7 (Japanese Unexamined Patent Publication (Kokai) No. 5-84,085), 10 µl of 10×reaction buffer #1, 10 µl each of 20 mM dNTP's, 1 µl (20 pmol) each of the primers C7S2 and C7AS2, and 1 µl of Pfu DNA polymerase (STRATAGENE: 2.5 U) were added and were reacted for 5 minutes at 95° C., 5 minutes at 50° C., and 3 minutes at 72° C. It was then reacted for 30 cycles of 1 minute at 94° C., 1 minute at 50° C., and 1 minute at 72° C., and finally heated at 72° C. for 5 minutes.

When this PCR reaction was electrophoresed on 3% NUSIEVE 3:1 agarose (FMC Bioproducts), a PCR product of about 350 bp was obtained.

The PCR product was excised from the gel, purified using the Gene Clean II kit (Bio 101), and was recovered into 10 µl of the TE solution (10 mM Tris-HCl, pH 7.5, 1 mM EDTA). To 5 µl of the recovered DNA were added 1 µl (50 ng/µl) of PGEM-T vector (Promega), 1 µl of 10×T4 DNA ligase buffer, 1 µl of T4 DNA ligase (Promega: 1 Weiss unit/µl), and 2 µl of sterilized distilled water, and was then reacted at 16° C. for 3 hours.

Using 5 µl of this reaction product, E. coli XL-1 blue was transformed according to the method of Inoue et al. (Inoue et al., Gene 96 (1990): 23–28) and was plated on an L-amp plate containing X-gal and IPTG, from which a white colony was selected to obtain a colony having the plasmid which is ampicillin-resistant and β galactosidase-deficient. This white colony was cultured overnight in 3 ml of the LB medium containing 50 µg/ml ampicillin, and the plasmid DNA was recovered using the plasmid automatic separation instrument (KURABO: PI-100). This plasmid DNA was cleaved with the restriction enzymes ApaI and SacI and a plasmid DNA containing the fragment of the desired length was selected.

The plasmid DNA obtained was purified using the WIZARD (TM) Minipreps DNA Purification System (Promega) according to the manufacturer's protocol. The purified DNA was reacted with T7 primer (Applied Biosystems) using the ABI PRISM (TM) Ready Reaction dyeDeoxy (TM) terminator cycle Sequencing Kit (Applied Biosystems) according to the method recommended by the manufacturer. This reaction product was analyzed using the 370 DNA Sequencer (Applied Biosystems) and the nucleotide sequence was determined. The clone having the correct sequence was designated as pGEM-C7N.

Then the DNA fragment of pGEM-C7N was integrated into an expression vector pAT-Trp having the TrpE promoter.

One µg of pGEM-C7N was cleaved with the restriction enzymes EcoRI and BamHI, and was electrophoresed on 3% NUSIEVE 3:1 agarose (FMC Bioproducts) to obtain a DNA fragment of about 350 bp. The DNA fragment was excised from the gel, purified using the GENE CLEAN II kit, and was recovered into 10 µl of the TE solution. To 5 µl of the recovered DNA fragment were added 1 µl (50 ng/µl) of an expression vector pAT-TrpE (Japanese Unexamined Patent Publication (Kokai) No. 5-84,085) having the Trp promoter which had been cleaved with the restriction enzymes EcoRI and BamHI, 1 µl of 10×T4 DNA ligase buffer, 1 µl of T4 DNA ligase (1 Weiss unit/µl), and 2 µl of sterilized distilled water, and then was reacted at 16° C. for 3 hours.

Using 5 µl of this reaction, E. coli XL-1 blue was transformed according to the method of Inoue et al. This colony was cultured overnight in 3 ml of the LB medium containing 50 µg/ml ampicillin, and the plasmid DNA was recovered using the plasmid automatic separation instrument (KURABO: PI-100). This plasmid DNA was cleaved with the restriction enzymes EcoRI and BamHI and the plasmid DNA containing the fragments of the desired length was selected.

The E. coli containing the desired plasmid was cultured overnight in the M9CA medium containing 100 µg/ml ampicillin, the E. coli was recovered, and the bacterial protein was recovered. The protein was run on SDS-PAGE and the agarose gel was stained with CBB to confirm the desired protein had a molecular weight of 14K.

The E. coli for which the expression was confirmed was cultured overnight in 3 liters of the M9CA medium containing 100 µg/ml ampicillin and the E. coli was recovered by centrifugation. One gram of E. coli was suspended in 5 ml of the lysis buffer (50 mM Tris-HCl, pH 8.0/30 mM NaCl/5 mM EDTA), and then 1 mg of lysozyme was added thereto, which was incubated under shaking at 37° C. for 1 hour. This was centrifuged at 15 K for 30 minutes at 4° C. to obtain a precipitate, to which was added Buffer A (50 mM Tris-HCl, pH 8.0) and suspended, and then was homogenized under the condition of 1500 rpm, 5 strokes.

This was centrifuged at 15 K for 15 minutes at 4° C., and the obtained precipitate was washed with Buffer A and was centrifuged again. To the obtained precipitate was added Buffer A containing 2 M urea and suspended thereinto, which was then centrifuged at 15 K for 15 minutes at 4° C. to obtain the supernatant and the precipitate. The precipitate was subjected to a similar procedure for 4 M and 6 M urea. After extraction with urea, the extract obtained by each procedure was run on SDS-PAGE electrophoresis and stained with CBB to confirm the fractions which contained the desired protein. The desired protein. was present together with contaminants in the extract of 4 M urea.

The 4 M urea extract was applied to Q Sepharose (16/10) and was eluted with 0–0.3 M NaCl at a flow rate of 0.4 ml/min for 15 minutes.

The eluted fraction showing the absorption peak at O.D. 280 nm was applied to Hiload Superdex 75 pg (26/60×2) in a gel filtration column and was eluted with Buffer B (50 mM sodium acetate, pH 5.5/4 M urea/0.2 M NaCl/5 mM DTT). Separation of the protein with SDS-PAGE confirmed that a substantially homogeneous protein was separated. The fraction in which the desired protein is present was dialyzed against 50 mM Tris-HCl, pH 8.0/0.4 M urea to remove DTT.

The purified antigen was evaluated for purity using SDS-PAGE.

The purified antigen was diluted to a concentration of 2.5 µg/ml in 0.1 M phosphate buffer, pH 7.5, containing 8 M urea. The diluted antigen was applied to a multi-module Nunc plate at an amount of 200 µl per well and allowed to stand at room temperature for 2 hours. After the antigen dilution solution was removed, 200 µl per well of the blocking solution (0.5% casein, 0.15 M NaCl, 2.5 mM EDTA, 0.1 M phosphate buffer, pH 7.0) was added and allowed to stand at room temperature for 2 hours.

Thus, the antigen was immobilized on the plate. Two hundred µl of the sample dilution solution was added to 200 µl of the sample, which was then added to the antigen-immobilized plate. After reacting at 30° C. for 1 hour, it was washed and the peroxidase-labelled anti-human IgG (mouse monoclonal antibody) was added thereto and was reacted at 30° C. for 1 hour. After washing, an o-phenylene diamine solution was added and was reacted at 30° C. for 1 hour. Then the reaction was stopped by adding 1 M sulfuric acid and the color development was measured at 492 nm using a photometer.

Identification of positiveness/negativeness was conducted by determining the positiveness identification value when the respective antigen was used from the distribution of the group (56 sera) consisting of the sera identified to be negative using the second generation HCV assay kit (Imuchek HCV Kokusai: Kokusai Shiyaku K. K.).

Out of the sera which were identified to be positive or negative, the group of sera (42 sera) identified to be positive using the second generation HCV detection reagent (Imuchek HCV Kokusai: Kokusai Shiyaku K. K.) was used. All of these sera exhibited positive reactivity for the C7 antigen. Positiveness of each antigen was C7-1 (9.5%), C7-2 (28.6%), C7-2 (28.6%), C7-3 (0%), C7-4 (0%), C7-5 (31.0%), C7-6 (11.9%), C7-46 (100%), and C7-Native (100%).

Example 3

Epitope Analysis of the C14-1-2 Antigen

The purified C14-1-2 peptide was diluted in 0.1 M phosphate buffer, pH 7.5, containing 8 M urea to a concentration of 2.5 μg/ml. The diluted antigen was applied to a multi-module plate of Nunc at an amount of 200 μl per well and allowed to stand at room temperature for 2 hours. After the antigen dilution solution was removed, 200 μl per well of the blocking solution (0.5% casein, 0.15 M NaCl, 2.5 mM EDTA, 0.1 M phosphate buffer, pH 7.0) was added and allowed to stand at room temperature for 2 hours. Thus the antigen was immobilized.

Twenty μl of the sample and 20 μl of the chemically synthesized peptide (0.1 mg/ml) were mixed in equal amounts and allowed to stand at room temperature for 1 hour. Two hundred μl of the sample dilution solution was added thereto, which was then added to the antigen-immobilized plate. After reacting at 30° C. for 1 hour, it was washed and the peroxidase-labelled anti-human IgG (mouse monoclonal antibody) was added thereto and reacted at 30° C. for 1 hour. After washing, the o-phenylene diamine solution was added and was reacted at 30° C. for 1 hour. Then the reaction was stopped by adding 1 M sulfuric acid and the color development was measured at 492 nm using a photometer.

TABLE 4

| Sample NO. | COI[1] Imuchek-HCV | Absorbance at 492 nm | | |
|---|---|---|---|---|
| | | trpE · C14-1-2 | Inhibiting peptide | trpE · C14-2-2 |
| CH 45 | 7.72< | 3.000< | (1 – Y) | 0.168 |
| CH 94 | 7.72< | 3.000< | (1 – Y = Z)[2] | 0.057 |
| LC 31 | 7.72< | 2.300 | (1 – Z > B > Y)[3] | 0.043 |
| HCC10 | 7.72< | 3.000< | (1 – Y) | 0.023 |
| HCC25 | 7.72< | 3.000< | (1 – Z = B)[4] | 0.268 |

TABLE 4-continued

| Sample NO. | COI[1] Imuchek-HCV | Absorbance at 492 nm | | |
|---|---|---|---|---|
| | | trpE · C14-1-2 | Inhibiting peptide | trpE · C14-2-2 |
| LC 25 | 7.72< | 1.750 | (1 – Z) | 0.049 |
| LC 92 | 7.72< | 0.554 | (1 – Z) | 0.004 |

Note:
[1] COI = cut off index
[2] 1 – Y = Z means that 1 – Y and 1 – Z give a similar degree of inhibition.
[3] 1 – Z > B > Y means that inhibition takes place for 1 – Z, 1 – Y, 1 – Z, with the intensity decreasing in the order of 1 – Z, 1 – B, and 1 – Y.
[4] 1 – Z = B means that 1 – Z and 1 – B give a similar degree of inhibition.

From the reactivity with trpE.C14-1-2 (Japanese Patent Application No. 5-194185) it is obvious that all the samples shown in Table 4 belong to the HCV group I and that reaction with trpE.C14-1-2 is inhibited by the addition of a peptide having the sequence of Group I. These results revealed that the epitope is present on the peptide which was inhibited by the antibody for the C14-1-2 antigen in the patient serum.

Example 4

Construction of the Gene Encoding an Epitope-chimera Antigen Peptide

DNAs shown in Table 5 were synthesized using the DNA synthesizer (ABI: Model 394A or Millipore: Model 8700).

TABLE 5

| | | |
|---|---|---|
| EPI: | GCGAATTCGCCTCACACCTCCCTTACATC | (SEQ ID NO: 16) |
| EP2R: | GGGTACCTACCACGGGAGCAGCAGCTC | (SEQ ID NO: 17) |
| CORE-F: | AGGTACCCCTAAAGCTCGTCGTCCGGAAGGTCGTGCT | (SEQ ID NO: 18) |
| CORE-R: | TCCCGGGTTGAGCCCAAGCACGACCTTCCGGACG | (SEQ ID NO: 19) |
| EP5: | ACCCGGGAGTGTGGTCATTGTGGGTAGG | (SEQ ID NO: 20) |
| EP6: | GAGGATCCTTATCAATCGAACTCCCGGTAGAGGACTTC | (SEQ ID NO: 21) |
| Gr1EPV5F: | GTAAGCTTCGCCTCACACCTCCCTTACATC | (SEQ ID NO: 22) |
| Gr1EPV5R: | GCCTCGAGAAAGAACTCCCGGTAGAGGAC | (SEQ ID NO: 23) |
| coreNF: | ATGGAGCTCGCCATGGGCATGGGCACGAAT | (SEQ ID NO: 24) |
| coreNR: | TATGGATCCTTATCTGGGGCCCCTGCGCGGCAA | (SEQ ID NO: 25) |
| C7EP1F: | CCAGCCTTCACTAAAGTGCCGGCTGCA | (SEQ ID NO: 26) |
| C7EP1R: | CTCTCCGGACCCTATGATGTCATAAGCGCC | (SEQ ID NO: 27) |
| C7EP2F: | GGGTCCGGAGAGGAGGTGGCCCTGTCT | (SEQ ID NO: 28) |
| C7EP2R: | GAAGCTTACCAGTCCAGATCCCTGGGTGACGCATCTGTTACA | (SEQ ID NO: 29) |
| GR2EP1F: | GACTCGAGGCCTCTAGAGCGGCTCTCATT | (SEQ ID NO: 30) |
| GR2EP1R: | GCTATCGATTTTTATGTCTTGGGCCTG | (SEQ ID NO: 31) |
| GR2EP2F: | AAAATCGATAGCTTGCATATCAACCAG | (SEQ ID NO: 32) |
| GR2EP2R: | GACGAGCTCCATCTCATCAAAAGCCTC | (SEQ ID NO: 33) |

TABLE 5-continued

| | | |
|---|---|---|
| COREGR2S: | CGGTCGACGGTACCCTGATTATTCCGAAAGATCGTCGCAGCACCGGTA | (SEQ ID NO: 34) |
| COREGR2AS: | GCTATCGATGAGGAAGCCCGGTTTACCCCAGCTTTTACCGGTGCTGCG | (SEQ ID NO: 35) |

EP1 and EP2R are primers for taking out the sequence encoding the peptide from position 1712—position 1750 from the HCV cDNA of Group 1. EP81 and EP6 are primers for taking out the sequence encoding the peptide from position 1678—position 1705 from the HCV cDNA of Group 1. C7EP1F and C7EP1R are primers for taking out the sequence encoding the peptide from position 1238—position 1313, C7EP2F and C7EP2R are primers for taking out the sequence encoding the peptide from position 1363—position 1460, and coreNF and coreNR are primers for taking out the sequence encoding the peptide from position 1—position 43.

GR2EP1F and GR2EP1R are primers for producing the sequence encoding the peptide from position 1716—position 1750 of Group 2 HCV, COREGR2S and COREGR2AS are primers for producing the sequence encoding the peptide from position 66—position 80 of Group 2 HCV, and GR2EP2F and GR2EP2R are primers for producing the sequence encoding the peptide from position 1690—position 1713 of Group 2 HCV.

Using these primers the sequences were taken out by PCR. The construction of each fragment will be explained hereinbelow. One ng of HCV cDNA (C6-79) (Japanese Unexamined Patent Publication (Kokai) No. 6-225,770) and 100 pmol of the primer (EP1 and EP2R, or EP5 and EP6) were added, and 100 µl of a reaction mixture was adjusted to obtain 10 mM Tris-HCl, pH 8.3, 2.5 mM MgCl2, 0.01% gelatin, 0.2 mM dNTP, and 2.5 U Taq DNA polymerase. A mineral oil was layered on the mixture and was subjected to a reaction for 25 cycles of 30 seconds at 94° C., 1 minute at 55° C., and 2 minutes at 72° C.

Furthermore, 2 µg each of CORE-F and CORE-R was added, and 100 µl of a reaction mixture was adjusted to be 10 mM Tris-HCl, pH 8.3, 2.5 mM $MgCl_2$, 0.01% gelatin, 0.2 mM dNTP, and 2.5 U Taq DNA polymerase. A mineral oil was layered on the mixture and was subjected to a reaction for 15 cycles of 30 seconds at 94° C., 1 minute at 50° C., and 2 minutes at 72° C. A portion of the reaction mixture was subjected to agarose gel electrophoresis to separate about 140 bp length of fragment from the combination of EP1 and EP2R, about 150 bp length of fragment from the combination of EP1 and V4XYZ, about 50 bp length of fragment from the combination of CORE-F and CORE-R, and about 100 bp length of fragment from the combination of EP5 and EP6.

The separated DNA fragment was recovered from the agarose gel into the TE solution using the MERMAID nucleic acid purification Kit (Bio101) according to the method recommended by the manufacturer. The recovered DNA fragment together with 25 ng of pGEM-T (Promega) vector was reacted in 20 µl of the reaction mixture (50 mM Tris-HCl, pH 7.5, 10 mM $MgCl_2$, 1 mM ATP, 10 mM DTT, T4 DNA ligase) at 16° C. for 1 hour. A portion of the reaction mixture was used to transform E. coli XL1-Blue (Stratagene) according to the method of Hanahan (DNA Cloning: A practical approach, ed. D. M. Glover, vol. 1, pp 109-, IRC press, 1885). Ampicillin-resistant colonies were selected therefrom and the DNA of the transformants was prepared by the minipreparation method, and was cleaved with restriction enzymes to select the transformants having plasmids in which both fragments have been circularized.

The plasmid DNA in which a fragment derived from EP1 and EP2 has been cloned was cleaved with KpnI and EcoRI, and then was electrophoresed to separate an about 140 bp fragment, which was recovered into the TE solution using the MERMAID nucleic acid purification Kit (Bio101) according to the method recommended by the manufacturer. The plasmid DNA in which a fragment derived from CORE-F and CORE-R has been cloned was cleaved with KpnI and SmaI, and then was electrophoresed to separate an about 60 bp fragment, which was recovered into the TE solution using the MERMAID nucleic acid purification Kit (Bio101) according to the method recommended by the manufacturer.

The recovered fragment and pT7T319U (Pharmacia) cleaved with EcoRI and SmaI were subjected to ligation reaction using T4 DNA polymerase and a portion of the reaction mixture was used to transform E. coli SURE (Stratagene). Ampicillin-resistant colonies were selected therefrom and the DNA of the transformants was prepared by the minipreparation method, and was cleaved with restriction enzymes to select the transformants having plasmids in which both fragments have been circularized.

The plasmid obtained was cleaved with SmaI and BamHI and was ligated using T4 DNA ligase to the MERMAID nucleic acid purification kit fragment recovered using the kit (Boi101) by separating 100 bp of fragment on electrophoresis after cleaving the plasmid DNA in which the fragment derived from EP5 and EP6 have been cloned with BamHI and SmaI. A portion of the reaction mixture was used to transform E. coli XL1-Blue (Stratagene). Ampicillin-resistant colonies were selected therefrom and the DNA of the transformants were prepared by the minipreparation method, and was cleaved with restriction enzymes to select the transformants having plasmids in which both fragments have been circularized.

Thus a plasmid having the Gr1EPV5 gene fragment was constructed. Ten µg of this plasmid was used in a PCR using 30 pmol each of Gr1EPV5F and Gr1EPV5R primers to amplify the sequence encoding the amino acids at positions (1712–1750; Group 1)—(66–80; Group 1)—(1678–1705; Group 1), and the amplified fragment was recovered using the QIAquick PCR purification kit (QIAGEN). The recovered fragment was cloned into the PGEM-T (Promega) vector. Thus, pGR1EPN having an about 250 bp fragment which can be excised with HindIII and XhoI was obtained.

Using GR2EP1F and GR2EP1R, or GR2EP2F and GR2EP2R, an about 120 bp fragment from GR2EP1F and GR2EP1R and an about 80 bp fragment from GR2EP2F and GR2EP2R could be amplified by PCR from the S14 strain HCV cDNA (Japanese Patent Application No. 4-207391 by the applicant of the present invention). Furthermore, 2 µg each of CORE-F and CORE-R was added, and 100 µl of a reaction mixture was adjusted to obtain 10 mM Tris-HCl, pH 8.3, 2.5 mM $MgCl_{21}$ 0.01% gelatin, 0.2 mM dNTP, and 2.5 U Taq DNA polymerase. A mineral oil was layered on the mixture and was subjected to a reaction for 15 cycles of 30 seconds at 94° C., 1 minute at 50° C., and 2 minutes at 72° C. to obtain a fragment of about 50 bp.

These fragments were cloned into pGEM-T (Promega) vector. The plasmid having the fragment obtained from GR2EP1F and GR2EP1R was cleaved with XhoI and ClaI, and the plasmid having the fragment obtained from GR2EP2F and GR2EP2R was cleaved with SacI and ClaI, and were separated into small fragments by agarose electrophoresis. The small fragments recovered using the MERMAID nucleic acid purification Kit (Boi101) and pBluescript II KS(+) cleaved with XhoI and SacI were ligated with ligase, and by transforming *E. coli* Xl1-blue the plasmid having an about 190 bp fragment was obtained which could be excised by cleaving with XhoI and SacI.

This plasmid was cleaved with ClaI, to which was ligated a fragment obtained by cleaving the plasmid having the sequence obtained from CORE-F and CORE-R with AccI and ClaI to obtain a plasmid pGR2EPN having the sequence encoding (1716–1750; Group 2)—(66–80; Group 2)—(1690–1713; Group 2).

Using C7EP1F and C7EP1R, or C7EP2F and C7EP2R, an about 220 bp fragment from GR2EP1F and GR2EP1R and an about 300 bp fragment from GR2EP2F and GR2EP2R could be amplified by PCR from 1 ng of the HCV cDNA (C11-7) (Japanese Patent Application No. 2-180889). These fragments were cloned into pGEM-T (Promega) vector. The fragment obtained from C7EP1F and C7EP1R was cleaved with EcoRI and BspE1 and the fragment obtained from GR2EP2F and GR2EP2R was cleaved with BspE1 and HindIII, and then were subjected to agarose electrophoresis to separate small fragments.

The small fragments recovered using the Mermaid Kit (Boi101) and pUC19 cleaved with XhoI and SacI were ligated with ligase, and by transforming *E. coli* XL1-blue a plasmid pC7EPN having an about 500 bp fragment encoding (1238–1313)—(1368–1460) was obtained which could be excised by cleaving with EcoRI and HindIII.

Using coreNF and coreNR, an about 120 bp fragment could be amplified from 1 ng of the HCV cDNA (C11-21) (Japanese Patent Application No. 2-413844). By cloning these fragments into pGEM-T (Promega) vector, a plasmid PCORE having an about 120 bp fragment was obtained which encodes 1–43 and which could be excised with SacI and BamHI.

By combining and joining the above gene fragments and by introducing them into the EcoRI and BamHI sites of pAT-Trp, a vector pCSON which permits expression of the chimera antigen gene comprising an alignment (1238–1313)—(1363–1460)—(1712–1750; Group 1)—(66–80; Group 1)—(1678–1705; Group 1)—(1716–1750; Group 2)—(66–80; Group 2)—(1690–1713; Group 2)—(1–43) was constructed. *E. coli* pC50N/XL1-blue containing this plasmid has been deposited with the National Institute of Bioscience and Human-Technology, Agency of Industrial Science and Technology, MITI, 1-3, Higashi 1-chome Tsukuba-shi Ibaraki-ken, 305, Japan, as FERM P-15380 on December 27, 1995; and transferred to an international deposition under the Budapest treaty as FERM BP-6215 on Dec. 24, 1997.

Example 5

Expression and Purification of an Epitope-chimera Antigen

The *E. coli* transformed with pC50N was cultured overnight at 37° C. in the LB medium containing 100 μg/ml ampicillin. This was inoculated at a concentration of 1% into M9-CA containing 100 μg/ml ampicillin. After culturing, the cell mass was collected by centrifugation, was resuspended in 50 ml of the Lysis solution (50 mM Tris-HCl, pH 8.5, 30 mM NaCl, 5 mM EDTA), 1 ml of the lysozyme solution (10 mg/ml Lysozyme) was added thereto, and was treated at 37° C. for 1 hour. The suspension was subjected to the sonication treatment (150 W, 90 seconds, twice) to disrupt the cells.

The insoluble fraction was recovered by centrifuging at 15000 rpm for 30 minutes at 4° C. The insoluble fraction was resuspended in 50 ml of the A solution (50 mM Tris-HCl, pH 8.5) containing 1% NP40 and was homogenized (5 strokes at 1500 rpm). The suspension was centrifuged at 15000 rpm for 30 minutes at 4° C. to recover the insoluble fraction. The insoluble fraction was resuspended in 50 ml of the A solution containing 2 M urea and was homogenized (5 strokes at 1500 rpm). The suspension was centrifuged at 15000 rpm for 30 minutes at 4° C. to recover the insoluble fraction. The insoluble fraction was resuspended in 50 ml of the A solution containing 6 M urea and was homogenized (5 strokes at 1500 rpm). The suspension was centrifuged at 15000 rpm for 30 minutes at 4° C. to recover the soluble fraction.

From the antigen solution solubilized with the solution containing 6 M urea, an epitope-chimera antigen was purified by the ion exchange method using S sepharose HP column (Pharmacia) and the gel filtration method using SUPERDEX 75pg (Pharmacia).

Example 6

Reaction of the Epitope-chimera Antigen with Patient Serum

The epitope-chimera antigen was diluted in 0.1 M phosphate buffer, pH 7.5, containing 8 M urea to a concentration of 3 μg/ml of purified antigen. The diluted antigen was applied to a multi-module Nunc plate at an amount of 200 μl per well and allowed to stand at room temperature for 2 hours. After the antigen dilution solution was removed, 200 μl per well of the blocking solution (0.5% casein, 0.15 M NaCl, 2.5 mM EDTA, 0.1 M phosphate buffer, pH 7.0) was added and allowed to stand at room temperature for 2 hours.

Thus the antigen was immobilized on the plate. To 20 μl of the sample was added 200 μl of the sample dilution solution, which was then added to the antigen-immobilized plate. After reacting at 30° C. for 1 hour, it was washed and the peroxidase-labelled anti-human IgG (mouse monoclonal antibody) was added thereto and was reacted at 30° C. for 1 hour. After washing, the o-phenylene diamine solution was added and was reacted at 30° C. for 1 hour. Then the reaction was stopped by adding 1 M sulfuric acid and the color development was measured at 492 nm using a photometer.

As the second generation HCV antibody detection reagent employing multiple antigens, Imuchek HCV Kokusai (International Reasent Corporation) and RIBA-2 (Ortho) were used and identification was conducted according to the criteria described in the respective kit inserts. The results are shown together.

A false positive sample such as serum No. 10 for which identification was different between the second generation reagents tested negative by the C50N antigen of the present invention and serum No. 14 which were indeterminate between the second generation reagents tested positive by the C50N antigen of the present invention.

Thus it is obvious that the CN50 antigen of the present invention, by a single antigen, exhibits the performance of the HCV antibody detection reagents which employs a combination of multiple antigens. The results are shown in Table 6 and Table 7.

Example 7

Construction and Expression of the Antigen Gene Having Artificial Sequences

The DNA fragments having the following sequences were synthesized using a DNA synthesizer (Applied Biosystems 394A) according to the method recommended by the manufacturer. The synthesized DNA fragments were purified using the OPC column (Applied Biosystems) according to the method recommended by the manufacturer.

```
EP-10:      AGCCGTGACC CAGAATTCAC CAAAGTGCCG GTTGCTTATG    (SEQ ID NO:48)
            CGGCCAAAGG TTATAAGGTC CTGGTTCTGG ACCCGAGC

EP-11:      ACCATGGGCC TTGCTCAGAT ACGCGCCGAA ACCCAGGGTG    (SEQ ID NO:49)
            CTGGCAACGC TCGGGTCCAG AACCAG

EP-12:      GCCCATGGTG TGAACCCGAA CATCCGCACG GGCATCCGTA    (SEQ ID NO:50)
            CCGTTACCAC CGGTGCTCCG GTGACCTAT

EP-13:      ATCGTACGCA CCGCCGGCGC AACCGCCGTC CGCCAGGTAT    (SEQ ID NO:51)
            TTACCGTAGG TGGAATAGGT CACCGGAGCA CC

EP-14:      GGTGCGTACG ATGTGATCTA TGGCCGCGCG ATCCCGATCG    (SEQ ID NO:52)
            AAGCGATCAA AGGCGGTCGC CATCTGGTT

EP-15:      CAATCCGGAC AGCGCGCTCG CCAGTTCATC GCATTTCTCC    (SEQ ID NO:53)
            TTGCTATGGC AGAAAACCAG ATGGCGACCG CC

EP-16:      CTGTCCGGAT TGGGTCTGAA CGCTGTGGCA TTCTATCGCG    (SEQ ID NO:54)
            GTCTGGACGT GAGCATTATC CCGACCCAGG GC

EP-17:      CGCGAAGCTT ACCAGACCGG TCATCACCGC ATCGGTGCTA    (SEQ ID NO:55)
            ACGATAACCA CATCGCCCTG GGTCGGGATA AT

EP-18:      GTAAGCTTCG CGAGCCATGT GCCGTACATC GAGCAGGGTA    (SEQ ID NO:56)
            TGCAACTGAG CGAACAATTT AAGCAGAAG

EP-19:      CGGGGCGGCC GCCTCCGCCT GTTGGTCGC GGTCTGCAGC     (SEQ ID NO:57)
            AGACCCAGGC TCTTCTGCTT AAATTGTTCG CT

E-20:       GAGGCGGCCG CCCCGGTGGT TGGCACCCCG AAAAGCCGCC    (SEQ ID NO:58)
            GTCCG

E-21:       GATGGTACCC GGTTGCGCCC AGGCACGACC TTCCGGACGG    (SEQ ID NO:59)
            CGGCTTTTC

CEP (13):   CAGGGTACCA TCATCCTGAG CGGTCGTCCG GCGGTTGTAC    (SEQ ID NO:60)
            CGGAT

CEP (14):   CTCGAGAAAT TCTTGATACA GCACTTCACG ATCCGGTACA    (SEQ ID NO:61)
            ACCGC

EP101:      GAGCTCGCCA TGGGCACCAA CCCGAAACCG CAGCGTAAAA    (SEQ ID NO:62)
            GCAAGCGTAA CACCAACCGT AAACCGCAGG ATATTAAA

EP102:      GCGGATCCTT ACGGACCACG ACGCGGCACC AGGTACACAC    (SEQ ID NO:63)
            CACCCACCAC CTGACCACTA CCCGGGAATT TAATATCCT
            GCGGTTTACG 42-1:       GGCCCTGTCT AACACTGGAG AGGTCCCCTT CTATGGCCGC    (SEQ ID NO:64)
            GCGATCCCGA T 42-2:       GGCCCTGTCT AACACTGGAG AGGTCCCCTT CTATGGCCGC    (SEQ ID NO:65)
            GCGATCCCGA T 42-3:       GTTACAGTCG ACCACTGAGT CAAAATCGCC GGTAAAACCG    (SEQ ID NO:66)
            GTCATCAGCG CATCGG 42-4:       CGAAGCTTAC CAGTCCAGAT CCCTGGGTGA TGCATGTGTT    (SEQ ID NO:67)
            ACAGTCGACC ACTGAGT
```

The C region epitope gene fragments were adjusted by combinations of EP-10 and EP-11, EP-12 and EP-13, EP-14 and EP-15, and CP-16 and EP-17 so that 100 µl of the reaction solution contains 1 µg each of the purified DNA fragments, and were reacted using Taq DNA polymerase (Perkin Elmer) for 15 cycles of 30 seconds at 94° C., 1 minute at 50° C., and 1 minute at 72° C. The fragments were separate on 3% agarose gel electrophoresis and the DNA fragments were recovered into the TE buffer using the MERMAID DNA purification kit (Boi101) according to the method recommended by the manufacturer. A portion of the recovered DNA fragment was subjected to a ligation reaction with the PGEM-T vector according to the method recommended by the manufacturer and, by transforming E. coli XL1-blue, each fragment was cloned.

After confirming that the nucleotide sequence is correct by the Automated DNA sequencer (Applied Biosystems 373A), the fragments obtained by cleaving with EcoRI-NcoI from the plasmid into which the fragments obtained from the combination of EP-10 and EP-11 have been cloned, the fragments obtained by cleaving with NcoI-BsiwI from the plasmid into which the fragments obtained from the combination of EP-12 and EP-13 have been cloned, the fragments obtained by cleaving with BsiwI-BspEI from the plasmid into which the fragments obtained from the combination of EP-14 and EP-15 have been cloned, and the fragments obtained by cleaving with BspEI-HindIII from the plasmid into which the fragments obtained from the combination of EP-16 and EP-17 have been cloned were prepared, which were then combined to construct an E. coli-HindIII fragment encoding the NS3 region epitope.

The fragments encoding the NS4 region epitope of the HCV Group 1 and the core region epitope of the HCV Group 1, in combinations with EP-18 and EP-19, and EP-20 and EP-21, were adjusted so that 100 μl of the reaction mixture contains 1 μg each of the purified DNA fragments, and were reacted using Taq DNA polymerase (Perkin Elmer) for 15 cycles of 30 seconds at 94° C., 1 minute at 50° C., and 1 minute at 72° C. The fragments were separated on 3% agarose gel electrophoresis and the DNA fragments were recovered into the TE buffer using the MERMAID-DNA purification kit (Boi101) according to the method recommended by the manufacturer. A portion of the recovered DNA fragment was subjected to a ligation reaction with the PGEM-T vector according to the method recommended by the manufacturer and, by transforming E. coli XL1-blue, each fragment was cloned.

After confirming that the nucleotide sequence is correct by a Automated DNA sequencer (Applied Biosystems 373A), the fragments obtained by cleaving with HindIII-NotI from the plasmid into which the fragments obtained from the combination of EP-18 and EP-19 have been cloned, and the NotI-KpnI fragments from the plasmid into which the fragments obtained from the combination of EP-20 and EP-21 have been cloned were prepared and, by ligating them, the HindIII-KpnI fragment was prepared. On the other hand, 100 μl of the reaction mixture was adjusted to contain 1 μg each of the purified DNA fragments of CEP (13) and CEP (14), and were reacted using Taq DNA polymerase (Perkin Elmer) for 15 cycles of 30 seconds at 94° C., 1 minute at 50° C., and 1 minute at 72° C.

The fragments were separated on 3% agarose gel electrophoresis and the DNA fragments were recovered into the TE buffer using the Mermaid DNA purification kit (Boi101) according to the method recommended by the manufacturer. A portion of the recovered DNA fragment was subjected to a ligation reaction with the pGEM-T vector according to the method recommended by the manufacturer and, by transforming E. coli XL1-blue, each fragment was cloned. After confirming that the nucleotide sequence is correct by the Automated DNA sequencer (Applied Biosystems 373A), the KpnI-XhoI fragments obtained from the plasmid into which the fragments obtained from the combination of CEP (13) and CEP (14) have been cloned were ligated to the above HindIII-KpnI fragment to obtain the HindIII-XhoI fragment encoding the Group 1 epitope chimera peptide.

The fragment used which encodes the Group 2 chimera peptide was the one obtained by cleaving pC50N with XhoI-SacI.

The fragments encoding these core epitope peptides were adjusted so that 100 μl of the reaction mixture contains 1 μg each of the purified EP101 fragment and EP102 fragment, and were reacted using Taq DNA polymerase (Perkin Elmer) for 15 cycles of 30 seconds at 94° C., 1 minute at 50° C., and 1 minute at 72° C. The fragments were separated on 3% agarose gel electrophoresis and the DNA fragments were recovered into the TE buffer using the MERMAID DNA purification kit (Boi101) according to the method recommended by the manufacturer.

A portion of the recovered DNA fragment was subjected to a ligation reaction with the pGEM-T vector according to the method recommended by the manufacturer and, by transforming E. coli XL1-blue, each fragment was cloned. After confirming that the nucleotide sequence is correct by the Automated DNA sequencer (Applied Biosystems 373A), the SacI-BamHI fragments encoding the core epitope peptide were obtained.

By sequentially ligating each of the epitope fragments, the EcoRi-BamHI fragments were obtained encoding the epitope chimera peptide CEP-A. By inserting the fragment into the E. coli-BamHI site of the pAT-TrpE vector, the CEP-A antigen expression vector pCEP-A was constructed.

The NS3 region of the expression plasmid of the CEP-A antigen was modified as follows:

To 1 μg (10 μl) of pCEP-A were added 5 μl of 10×LA PCR Buffer, 5 μl of 2 mM dNTP, 0.2 μl each of the primers 42-2 and 42-3 (100 pmol/μl), and 0.5 μl of TaKaRa LA Taq (Takara Shuzo, 5 units/μl), which was made to 50 μl with sterilized distilled water. One drop of a mineral oil (Sigma) was layered thereon, and after stirring it was gently centrifuged. This was applied to the DNA Thermal cycler PJ2000 of Perkin Elmer Cetus to conduct a PCR reaction. The reaction profile comprised 30 cycles of DNA denaturation at 94° C. for 0.5 minute, annealing at 50° C. for 1 minute, and elongation at 72° C. for 1 minute. After the reaction it was retained at 72° C. for 7 minutes and then cooled to 4° C.

To 2.5 μl of the PCR reaction mixture were added 5 of 10×LA PCR Buffer, 5 μl of 2 mM dNTP, 0.2 μl each of the primers 42-2 and 42-3 (100 pmol/μl), and 0.5 μl of TaKaRa LA Taq (Takara Shuzo, 5 units/μl), which was made to 50 μl with sterilized distilled water. This was applied to the DNA Thermal cycler PJ2000 of Perkin Elmer Cetus to conduct a PCR reaction. The reaction profile comprised 30 cycles of DNA denaturation at 94° C. for 0.5 minute, annealing at 50° C. for 1 minute, and elongation at 72° C. for 1 minute. After the reaction it was retained at 72° C. for 7 minutes and then cooled to 4° C. When the PCR reaction mixture was electrophoresed on 3% NUSIEVE agarose (FMC Bioproducts), a PCR product of about 350 bp was obtained.

This PCR product of about 350 bp, excised from agarose, to which 200 μl of TE (10 mM Tris-HCl, pH 7.5, 1 mM EDTA) was added, was heated to 68° C. Phenol extraction was conducted twice with TE-saturated phenol and chloroform extraction was conducted twice with TE-saturated chloroform, and the aqueous phase was separated. It was precipitated with ethanol and rinsed once with 75% ethanol, dried, and dissolved in 10 μl of TE. To 5 μl of the recovered DNA were added 1 μl of the PGEM-T vector (Promega), 1 μl of 10×T4 DNA ligase buffer, 1 μl of T4 DNA ligase (Promega: 1 Weiss unit/μl), and 2 μl of sterilized distilled water, and the mixture was reacted at 16° C. for 1 hour.

Using 5 μl of this reaction mixture, E. coli XL-1 blue was transformed according to the method of Inoue et al. (Inoue et al., Gene 96 (1990): 23–28) and was plated on the LB-amp plate containing X-gal and IPTG, from which a white colony was selected to obtain a colony having the plasmid which is ampicillin-resistant and β galactosidase-deficient. This white colony was cultured overnight in 3 ml of the LB medium containing 100 μg/ml ampicillin, and the plasmid DNA was recovered using the plasmid automatic separation instrument (KURABO: PI-100). This plasmid DNA was cleaved with the restriction enzymes SpiI and HindIII and the plasmid DNA containing the fragments of the desired length was selected.

The plasmid DNA obtained was purified using the WIZARD (TM) Minipreps DNA Purification System (Promega) according to the manufacturer's protocol. The purified DNA was reacted with T7 primer and SP6 primer (Applied Biosystems) using the ABI PRISM (TM) Ready Reaction dyeDeoxy (TM) terminator cycle Sequencing Kit (Applied Biosystems) according to the method recommended by the manufacturer. This reaction product was analyzed using a 370 DNA Sequencer (Applied Biosystems) and the nucleotide sequence was determined. The clone having the correct sequence was designated as pGEM-C7M.

pGEM-C7M was cleaved with SpiI and HindIII, and was electrophoresed to obtain a fragment of about 340 bp. Using the MERMAID DNA purification kit (Boi101) the separated fragment was recovered into the TE buffer according to the method recommended by the manufacturer. On the other hand, CEP-A was cleaved with Sp1I and HindIII and an about 4 kbp fragment was separated by agarose electrophoresis. Using the GENE CLEAN II kit (Boi101) the separated fragment was recovered into the TE buffer according to the method recommended by the manufacturer. Both of the recovered fragments were ligated by Taq DNA polymerase. Using the reaction mixture E. coli HB101 was transformed and the clone in which the desired fragment has been inserted was selected.

As a result, an E. coli transformant CEPM/HB101 strain which was transformed by the expression vector pCEPM expressing the antigen CEPM comprising the epitope fragment (1238–1313 ; Group 1-like)—(1363–1460; Group 1-like)—(1712–1751; Group 1-like)—(66–80; Group 1-like)—(1686–1704; Group 1-like)—(1716–1751; Group 2)—(66–80; Group 2)—(1690–1713; Group 2)—(1–42; Group 1-like) was obtained.

Example 8

Expression and Purification of an Epitope-chimera Antigen

The E. coli transformant CEPM/HB101 strain was cultured overnight at 37° C. in the LB medium containing 100 μg/ml ampicillin. This was inoculated at a concentration of 1% into M9-CA containing 100 μg/ml ampicillin and cultured overnight at 37° C. After culturing the cell mass was collected by centrifugation, was resuspended in 50 ml of the Lysis solution (50 mM Tris-HCl, pH 8.5, 30 mM NaCl, 5 mM EDTA), 1 ml of the lysozyme solution (10 mg/ml Lysozyme) was added thereto, and treated at 37° C. for 1 hour. The suspension was subjected to sonication treatment (150 W, 90 seconds, twice) to disrupt the cells. The insoluble fraction was recovered by centrifuging at 15000 rpm for 30 minutes at 4° C.

The insoluble fraction was resuspended in 50 ml of the A solution (50 mM Tris-HCl, pH 8.5) containing 1% NP40 and was homogenized (5 strokes at 1500 rpm). The suspension was centrifuged at 15000 rpm for 30 minutes at 4° C. to recover the insoluble fraction. The insoluble fraction was resuspended in 50 ml of the A solution containing 2 M urea and was homogenized (5 strokes at 1500 rpm). The suspension was centrifuged at 15000 rpm for 30 minutes at 4° C. to recover the insoluble fraction. The insoluble fraction was resuspended in 50 ml of the A solution containing 6 M urea and was homogenized (5 strokes at 1500 rpm). The suspension was centrifuged at 15000 rpm for 30 minutes at 4° C. to recover the soluble fraction.

From the antigen solution solubilized with a solution containing 6 M urea, the epitope-chimera antigen of the present invention was purified by the ion exchange method using S sepharose HP column (Pharmacia) and the gel filtration method using SUPERDEX 75pg (Pharmacia).

Example 9

Reaction of the Epitope-chimera Antigen with Patient Serum

The epitope-chimera antigen CEPM of the present invention obtained as described above was diluted in 0.1 M phosphate buffer, pH 7.5, containing 8 M urea to a concentration of 5 μg/ml. The diluted antigen was applied to a multi-module Nunc plate at an amount of 200 μl per well and allowed to stand at room temperature for 2 hours. After the antigen dilution solution was removed, 200 μl per well of the blocking solution (0.5% casein, 0.15 M NaCl, 2.5 mM EDTA, 0.1 M phosphate buffer, pH 7.0) was added and allowed to stand at room temperature for 2 hours. Thus the antigen was immobilized on the plate. To 20 μl of the sample was added 200 μl of the sample dilution solution, which was then added to the antigen-immobilized plate.

After reacting at 30° C. for 1 hour, it was washed and the peroxidase-labelled anti-human IgG (mouse monoclonal antibody) was added thereto and was reacted at 30° C. for 1 hour. After washing, the o-phenylene diamine solution was added and was reacted at 30° C. for 1 hour. Then the reaction was stopped by adding 1 M sulfuric acid solution and the color development was measured at 492 nm using a photometer.

The results are shown in Table 6 and Table 7.

TABLE 6

| 2nd generation reagent | C50N antigen | CEPM antigen | 2nd generation definitive diagnosis | | | |
|---|---|---|---|---|---|---|
| Titer | Absorbance | Absorbance | 5-1-1 | C100-3 | C33 | C22 |
| 0.00 | 0.019 | 0.001 | 0 | 0 | 0 | 0 |
| 0.01 | 0.018 | 0.054 | 0 | 0 | 0 | 0 |
| 0.22 | 0.022 | 0.025 | 0 | 0 | | |
| 0.04 | 0.024 | 0.018 | 0 | 0 | | |
| 0.04 | 0.018 | 0.009 | 0 | 0 | | |
| 0.04 | 0.030 | 0.011 | 0 | 0 | 0 | 0 |
| 0.04 | 0.013 | 0.004 | 0 | 0 | | |
| 0.00 | 0.025 | 0.005 | 0 | 0 | | |
| 0.01 | 0.019 | 0.001 | 0 | 0 | 0 | 0 |
| 1.21 | 0.042 | 0.013 | 0 | 0 | 0 | 0 |
| 0.01 | 0.020 | 0.027 | 0 | 0 | 0 | 0 |
| 0.01 | 0.190 | 0.132 | 0 | 0 | 0 | 0 |
| 0.07 | 0.020 | 0.017 | 0 | 0 | 0 | 0 |
| 10.20 | 2.939 | 2.125 | 0 | 0 | 0 | 4 |
| 0.05 | 0.018 | 0.003 | 0 | 0 | 0 | 0 |
| 0.16 | 0.030 | 0.028 | 0 | 0 | | |
| 0.00 | 0.011 | 0.001 | 0 | 0 | | |
| 11.50 | 2.964 | 2.978 | 0 | 0 | 4 | 4 |
| 8.60 | 3.000 | 3.000 | 4 | 4 | 4 | 4 |
| 8.60 | 3.000 | 3.000 | 4 | 3 | 4 | 4 |
| 8.60 | 3.000 | 3.000 | 4 | 4 | 4 | 4 |
| 8.60 | 3.000 | 3.000 | 3 | 4 | 4 | 4 |
| 8.60 | 3.000 | 3.000 | 4 | 4 | 4 | 4 |
| 8.60 | 3.000 | 2.619 | 3 | 0 | 4 | 4 |
| 8.60 | 3.000 | 2.204 | 3 | 4 | 4 | 4 |
| 10.10 | 3.000 | 3.000 | 4 | 4 | 4 | 4 |

TABLE 7

| 2nd generation reagent | C50N antigen | CEPM antigen | 2nd generation definitive diagnosis | | | |
|---|---|---|---|---|---|---|
| Titer | Absorbance | Absorbance | 5-1-1 | C100-3 | C33 | C22 |
| 10.10 | 3.000 | 3.000 | 4 | 4 | 4 | 4 |
| 10.10 | 3.000 | 3.000 | 4 | 2 | 4 | 4 |
| 10.10 | 3.000 | 3.000 | 0 | 0 | 3 | 4 |
| 10.10 | 3.000 | 3.000 | 4 | 4 | 4 | 4 |
| 10.10 | 3.000 | 3.000 | 4 | 4 | 4 | 4 |
| 10.10 | 3.000 | 3.000 | 3 | 4 | 4 | 4 |
| 11.60 | 3.000 | 3.000 | 2 | 3 | 4 | 4 |
| 11.60 | 3.000 | 0.007 | 3 | 4 | 4 | 4 |
| 0.10 | 0.018 | 0.001 | 0 | 0 | 0 | 0 |
| 0.04 | 0.012 | 0.026 | 0 | 0 | 0 | 0 |
| 0.06 | 0.012 | 0.037 | 0 | 0 | 0 | 0 |
| 0.06 | 0.028 | 0.007 | 0 | 0 | 0 | 0 |
| 0.04 | 0.009 | 0.004 | 0 | 0 | 0 | 0 |
| 0.04 | 0.015 | 0.007 | 0 | 0 | 0 | 0 |
| 0.08 | 0.025 | 0.014 | 0 | 0 | 0 | 0 |
| 0.05 | 0.012 | 0.016 | 0 | 0 | 0 | 0 |
| 0.08 | 0.017 | 0.008 | 0 | 0 | 0 | 0 |
| 11.60 | 2.969 | 2.991 | 4 | 4 | 4 | 4 |
| 11.60 | 3.000 | 3.000 | 3 | 4 | 4 | 4 |
| 11.60 | 3.000 | 3.000 | 4 | 4 | 4 | 4 |
| 9.30 | 1.861 | 0.595 | 1 | 0 | 2 | 0 |
| 7.40 | 3.000 | 2.860 | 0 | 0 | 2 | 4 |
| 9.60 | 3.000 | 1.624 | 4 | 4 | 4 | 0 |

What is claimed is:

1. A hepatitis C virus (HCV) chimeric antigen peptide that specifically binds to antibodies produced by an HCV-infected human consisting of:
    a) the peptide region of the HCV NS3 region shown as position 1–74 or 1–76 of SEQ ID NO:39, the peptide region of the HCV NS3 region shown as position 1–98 of SEQ ID NO:40, the peptide region of the HCV NS4 region show as position 1–39 of SEQ ID NO:41, the peptide region of the HCV Core region shown as position 1–15 of SEQ ID NO:37, and the peptide region of the HCV NS4 region shown as position 9–27 of SEQ ID NO:42 of the HCV polypeptide belonging to the genotype group 1;
    b) the peptide region of the HCV NS4 region shown as position 1–36 of SEQ ID NO:43, the peptide region of the HCV Core region shown as position 1–15 of SEQ ID NO:38, and the peptide region of the HCV NS4 region shown as position 1–24 of SEQ ID NO:44 of the HCV polypeptile belonging to the genotype group 2; and
    c) the peptide region of the HCV Core region shown as position 1 to position 43 or from position 1 to position 42 of SEQ ID NO: 36, the HCV polypeptide belonging to the genotype group 1 or 2, wherein the above regions may be joined by a linker peptide having no epitope activity.

2. The HCV chimeric antigen peptide according to claim 1 wherein said NS3 epitopic region is located amino terminal to said NS4 and Core epitopic peptide regions.

3. A DNA encoding an HCV chimeric antigen peptide according to claim 2.

4. A method of producing a chimera antigen peptide, said method comprising:
    a) growing host cells containing an expression vector, said vector containing the DNA of claim 3 under conditions whereby the chimeric antigen peptide encoded by the DNA is expressed by the lost cells; and
    b) harvesting the chineric antigen peptide produced by the host cells.

5. A method of detecting HCV infection by detecting the presence of antibodies present in an individual that bind to one or more HCV epitopic peptide regions, said method comprising:
    a) contacting a test sample from an individual suspected of being infected with HCV with the chimeric antigen peptide of claim 1 under conditions that allow binding of antibodies to HCV epitopic peptide regions; and
    b) determining whether antibodies from the rest sample are bound to the chimeric antigen peptide, whereby the presence of bound antibodies indicates the detection of HCV infection.

6. The HCV chimeric antigen peptide according to claim 1 wherein the epitopic peptide regions of the Core are the sequence of amino acids shown as residues 1–40, 1–42 or 1–43 of SEQ ID NO: 36 and the sequence of amino acids shown as residues 1–15 of SEQ ID NO:37, and 1–15 of SEQ ID NO:38.

7. The HCV chimeric antigen peptide according to claim 1 wherein the epitopic peptide regions of NS3 are the sequence of amino acids shown as residues 1–74 or 1–76 of SEQ ID NO: 39, and the sequence of amino acids shown as residues 1–98 or 4–98 of SEQ ID NO: 40.

8. The HCV chimeric antigen peptide according to claim 1 wherein the epitopic peptide regions of NS4 are the sequence of amino acids shown as residues 1–39 of SEQ ID NO: 41, the sequence of amino acids shown as residues 9–27 of SEQ ID NO:42, the sequence of amino acids shown as residues 1–35 or 1–36 of SEQ ID NO:43, and the sequence of amino acids shown as residues 1–24 of SEQ ID NO:44.

9. The HCV chimeric antigen peptide according to claim 2, wherein said NS3 epitopic peptide region is SEQ ID NO:39 and wherein sequence ID NO:39 is separated from the N-terminus of the chimeric antigen peptide by amino acid residues 1–17 of SEQ ID NO:1 or residues 1–2 of SEQ ID NO:47.

10. A hepatitis C virus (HCV) chimeric antigen peptide that specifically binds to antibodies produced by an HCV-infected human comprising:
   a) the peptide region is an HCV NS3 segment shown as position 1–74 or 1–76 of SEQ ID NO:39, an HCV NS3 segment shown as position 1–98 of SEQ ID NO:40, an HCV NS4 segment shown as position 1–39 of SEQ ID NO:41, an HCV Core segment shown as position 1–15 of SEQ ID NO:37, and an HCV NS4 segment shown as position 9–27 of SEQ ID NO:42 of the HCV polypeptide belonging to the genotype group 1;
   b) the peptide region comprising an HCV NS4 segment shown as position 1–36 of SEQ ID NO:43, an HCV Core segment shown as position 1–15 of SEQ ID NO:38, and an HCV NS4 segment shown as position 1–24 of SEQ ID NO:44 of the HCV polypeptide belonging to the genotype group 2; and
   c) the peptide region comprising an HCV Core segment shown as position 1 to position 43 or from position 1 to position 42 of SEQ ID NO: 36, and the HCV polypeptide belonging to the genotype group 1 or 2, wherein the above regions may be joined by a linker peptide having no epitope activity.

11. The HCV chimeric antigen peptide according to claim 10 wherein said NS3 segment is located amino terminal to said NS4 and core peptide segments.

12. A DNA encoding an HCV chimeric antigen peptide according to claim 10.

13. A method of producing a chimeric antigen peptide, said method comprising
   a) growing host cells containing an expression vector, said vector containing the DNA of claim 12 under conditions whereby the chimeric antigen peptide encoded by the DNA is expressed by the host cells; and
   b) harvesting the chimeric antigen peptide produced by the host cell.

14. A method of detecting HCV infection by detecting the presence of antibodies present in an individual that bind to one or more HCV epitopic peptide segments, said method comprising:
   a) contacting a test sample from an individual suspected of being infected with HCV with the chimeric antigen peptide of claim 10 under conditions that allow binding of antibodies to HCV epitopic peptide segments; and
   b) determining whether antibodies from the test sample are bound to the chimeric antigen peptide, whereby the presence of bound antibodies indicates the detection of HCV infection.

15. The HCV chimeric antigen peptide according to claim 10 wherein said Core epitopic segment is the sequence of amino acids showing as residues 1–40, 1–42 or 1–43 of SEQ ID NO: 36 and the sequence of amino acids shown as residues 1–15 of SEQ ID NO;37, and 1–15 of SEQ ID NO:38.

16. The HCV chimeric antigen peptide according to claim 10 wherein said NS3 epitopic segment is the sequence of amino acids shown as residues 1–74 or 1–76 of SEQ ID NO: 36 and the sequence of amino acids shown as residues 1–98 or 4–98 of SEQ ID NO: 40.

17. The HCV chimeric antigen peptide according to claim 10 wherein said NS4 epitopic segment is the sequence of amino acids shown as residues 1–39 of SEQ ID NO: 41, the sequence of amino acids shown as residues of SEQ ID NO:42, the sequence of amino acids shown as residues 1–35 or 1–36 of SEQ ID NO:43, and the sequence of amino acids shown as residues 1–24 of SEQ ID NO:44.

18. The HCV chimeric antigen peptide according to claim 11, wherein said NS3 epitopic segment is SEQ ID NO:39 and wherein sequence ID NO:39 is separated from the N-terminus of the chimeric antigen peptide by amino acid residues 1–17 of SEQ ID NO:1 or residues 1–2 of SEQ ID NO:47.

19. The HCV chimeric antigen peptide according to claim 10, wherein said peptide comprises the amino acid sequence selected from the group consisting of SEQ ID NO:1 and SEQ ID NO: 47.

* * * * *